US009133469B1

(12) United States Patent
Hildebrand et al.

(10) Patent No.: US 9,133,469 B1
(45) Date of Patent: Sep. 15, 2015

(54) METHODS FOR INCREASING RENEWABLE OIL PRODUCTION

(75) Inventors: David Hildebrand, Lexington, KY (US); Runzhi Li, Lexington, KY (US); Tomoko Hatanaka, Kobe (JP)

(73) Assignee: University of Kentucky Research Foundation, Lexington, KY (US)

( * ) Notice: Subject to any disclaimer, the term of this patent is extended or adjusted under 35 U.S.C. 154(b) by 959 days.

(21) Appl. No.: 13/206,361

(22) Filed: Aug. 9, 2011

Related U.S. Application Data

(60) Provisional application No. 61/371,936, filed on Aug. 9, 2010.

(51) Int. Cl.
    *C12N 15/82* (2006.01)
(52) U.S. Cl.
    CPC .................................. *C12N 15/8247* (2013.01)
(58) Field of Classification Search
    None
    See application file for complete search history.

(56) References Cited

U.S. PATENT DOCUMENTS 7,511,189 B2 * 3/2009 Zou et al. .................. 800/281

OTHER PUBLICATIONS

Yu et al, Phytochemistry 69:1119-1127, 2008.*
Cases, S., S.J. Stone, P. Zhou, E. Yen, B. Tow, K.D. Lardizabal, T. Voelker, and R.V. Farese, Jr. 2001. Cloning of DGAT2, a second mammalian diacylglycerol acyltransferase, and related family members. J Biol Chem 276:38870-6.
Dahlqvist, A., U. Stahl, M. Lenman, A. Banas, M. Lee, L. Sandager, H. Ronne, and S. Stymne. 2000. Phospholipid:diacylglycerol acyltransferase: an enzyme that catalyzes the acyl-CoA-independent formation of triacylglycerol in yeast and plants. Proc Natl Acad Sci U S A 97:6487-92.
Dewey, R.E., R.F. Wilson, W.P. Novitzky, and J.H. Goode. 1994. The AAPT1 Gene of Soybean Complements a Cholinephosphotransferase-Deficient Mutant of Yeast. Plant Cell 6:1495-1507.
Lehner, R., and A. Kuksis. 1993. Triacylglycerol synthesis by an sn-1,2(2,3)-diacylglycerol transacylase from rat intestinal microsomes. J Biol Chem 268:8781-6.
Nosarzewski, M., and D.D. Archbold. 2007. Tissue-specific expression of Sorbitol Dehydrogenase in apple fruit during early development. J Exp Bot 58:1863-1872.
Oelkers, P., A. Tinkelenberg, N. Erdeniz, D. Cromley, J.T. Billheimer, and S.L. Sturley. 2000. A Lecithin Cholesterol Acyltransferase-like Gene Mediates Diacylglycerol Esterification in Yeast. J. Biol. Chem. 275:15609-15612.
Zou, J.T., V. Katavic, E.M. Giblin, D.L. Barton, S.L. Mackenzie, W.A. Keller, X. Hu, and D.C. Taylor. 1997. Modification of seed oil content and acyl composition in the Brassicaceae by expression of a yeast sn-2 acyltransferase gene. Plant Cell 9:909-923.
Bates, P.D., T.P. Durrett, J.B. Ohlrogge, and M. Pollard. 2009. Analysis of Acyl Fluxes through Multiple Pathways of Triacylglycerol Synthesis in Developing Soybean Embryos. Plant Physiol. 150:55-72.
Baud, S., and L. Lepiniec. 2009. Regulation of de novo fatty acid synthesis in maturing oilseeds of Arabidopsis. Plant Physiology and Biochemistry 47:448-455.
Baud, S., S. Wuilleme, A. To, C. Rochat, and L. Lepiniec. 2009. Role of WRINKLED1 in the transcriptional regulation of glycolytic and fatty acid biosynthetic genes in Arabidopsis. Plant Journal 60:933-947.
Cases, S., S.J. Smith, Y. Zheng, H.M. Myers, S.R. Lear, E. Sande, S. Novak, C. Collins, C.B. Welch, A.J. Lusis, S.K. Erickson, and R.V. Farese, Jr. 1998. Identification of a gene encoding an acyl CoA:diacylglycerol acyltransferase, a key enzyme in triacylglycerol synthesis. Proceedings of the National Academy of Sciences of the United States of America 95:13018-13023.
Cernac, A., and C. Benning. . 2004. WRINKLED1 encodes an AP2/EREB domain protein involved in the control of storage compound biosynthesis in Arabidopsis. . The Plant Journal 40:575-585.
Clemente, T. E., Cahoon, E. B., 2009. Soybean Oil: Genetic Approaches for Modification of Functionality and Total Content. Plant Physiol. 151, 1030-1040.
Dahmer, M.L., G.B. Collins, and D.F. Hildebrand. 1991. Lipid concentration and composition of soybean zygotic embryos maturing in vitro and in planta. Crop Sci. 31:735-740.
Andrianov, V., N. Borisjuk, N. Pogrebnyak, A. Brinker. J. Dixon, S. Spitsin, J. Flynn, P. Matyszczuk, K. Andryszak, M. Laurelli, M. Golovkin, and H. Koprowski. Tobacco as a production platform for biofuel: overexpression of Arabidopsis DGAT and LEC2 genes increases accumulation and shifts the composition of lipids in green biomass. Plant Biotechnology Journal (2010) 8, pp. 277-287.
Egli, D.B. 2008a. Comparison of corn and soybean yields in the United States: Historical trends and future prospects. Agron. J. 100:S79-S80.
Egli, D.B. 2008b. Soybean yield trends from 1972 to 2003 in midwestern USA. Field Crops Res. 106:53-59.
Focks, N., and C. Benning. 1998. wrinkled1: A Novel, Low-Seed-Oil Mutant of Arabidopsis with a Deficiency in the Seed-Specific Regulation of Carbohydrate Metabolism. Plant Physiol. 118:91-101.
Hiramine, Y., H. Emoto, S. Takasuga, and R. Hiramatsu. 2010. Novel acyl-coenzyme A:monoacylglycerol acyltransferase (MGAT) plays an important role in hepatic triacylglycerol secretion. J. Lipid Res. 51:1424-1431.
Hiraoka, M., A. Abe, and J.A. Shayman. 2002. Cloning and Characterization of a Lysosomal Phospholipase A2, 1-O-Acylceramide Synthase. J. Biol. Chem. 277:10090-10099.

(Continued)

*Primary Examiner* — Elizabeth McElwain
(74) *Attorney, Agent, or Firm* — Stites & Harbison PLLC; Terry L. Wright

(57) ABSTRACT

Methods of increasing renewable oil production are provided and include transforming a plant cell with an isolated nucleic acid encoding a *Vernonia galamensis* diacylglycerol acyltransferase (VgDGAT) polypeptide, where the expression of the VgDGAT polypeptide increases an amount of renewable oil in the plant. Transgenic plant cells comprising an isolated nucleic acid encoding a *Vernonia galamensis* diacylglycerol acyltransferase 1 (VgDGAT1) polypeptide are further provided.

35 Claims, 6 Drawing Sheets

(56) References Cited

OTHER PUBLICATIONS

Hobbs, D.H., and M.J. Hills. 2000. Expression and characterization of diacylglycerol acyltransferase from Arabidopsis thaliana in insect cell cultures. Biochem Soc Trans 28:687-9.
Hobbs, D.H., C. Lu, and M.J. Hills. 1999. Cloning of a cDNA encoding diacylglycerol acyltransferase from Arabidopsis thaliana and its functional expression. FEBS Lett 452:145-9.
Jackson, F.M., L. Michaelson, T.C.M. Fraser, A.K. Stobart, and G. Griffiths. 1998. Biosynthesis of triacylglycerol in the filamentous fungus Mucor circinelloides. Microbiology 144:2639-2645.
Kalinski, A., D.S. Loer, J.M. Weisemann, B.F. Matthews, and E.M. Herman. 1991. Isoforms of soybean seed oil body membrane protein 24 kDa oleosin are encoded by closely related cDNAs. Plant-molecular-biology 17:1095-8.
Kamisaka, Y., S. Mishra, and T. Nakahara. 1997. Purification and characterization of diacylglycerol acyltransferase from the lipid body fraction of an oleaginous fungus. J Biochem 121:1107-14.
Katavic, V., D.W. Reed, D.C. Taylor, E.M. Giblin, D.L. Barton, J. Zou, S.L. Mackenzie, P.S. Covello, and L. Kunst. 1995. Alteration of seed fatty acid composition by an ethyl methanesulfonate-induced mutation in Arabidopsis thaliana affecting diacylglycerol acyltransferase activity. Plant Physiol 108:399-409.
Lardizabal, K., R. Effertz, C. Levering, J. Mai, M.C. Pedroso, T. Jury, E. Aasen, K. Gruys, and K. Bennett. 2008. Expression of Umbelopsis ramanniana DGAT2A in Seed Increases Oil in Soybean. Plant Physiol. 148:89-96.
Le, B.H., J.A. Wagmaister, T. Kawashima, A.Q. Bui, J.J. Harada, and R.B. Goldberg. 2007. Using genomics to study legume seed development. Plant Physiology 144:562-574.
Vogel, G., and J. Browse. 1996. Cholinephosphotransferase and diacylglycerol acyltransferase: Substrate specificities at a key branch point in seed lipid metabolism. Plant physiol 110:923-931.
Li, R., K Yu, and D. Hildebrand. 2010a. DGAT1, DGAT2 and PDAT Expression in Seeds and Other Tissues of Epoxy and Hydroxy Fatty Acid Accumulating Plants. Lipids 45:145-157.
Loer, D.S., and E.M. Herman. 1993. Cotranslational integration of soybean (Glycine max) oil body membrane protein oleosin into microsomal membranes. Plant-physiology; Mar. 1993; 101(3): 993-998 101:993-998.
Lonien, J., and J. Schwender. 2009. Analysis of Metabolic Flux Phenotypes for Two Arabidopsis Mutants with Severe Impairment in Seed Storage Lipid Synthesis. Plant Physiol. 151:1617-1634.
Lu, C., and M.J. Hills. 2002. Arabidopsis mutants deficient in diacylglycerol acyltransferase display increased sensitivity to abscisic acid, sugars, and osmotic stress during germination and seedling development. Plant Physiol 129:1352-1358.
Lu, C., Z. Xin, Z. Ren, M. Miquel, and J. Browse. 2009. An enzyme regulating triacylglycerol composition is encoded by the ROD1 gene of Arabidopsis. Proceedings of the National Academy of Sciences 106:18837-18842.
Lu, C.L., S.B. De Noyer, D.H. Hobbs, J. Kang, Y. Wen, D. Krachtus, and M.J. Hills. 2003. Expression pattern of diacylglycerol acyltransferase-1, an enzyme involved in triacylglycerol biosynthesis, in Arabidopsis thaliana. Plant Mol Biol 52:31-41.
Maeo, K., T. Tokuda, A. Ayame, N. Mitsui, T. Kawai, H. Tsukagoshi, S. Ishiguro, and K. Nakamura. 2009. An AP2-type transcription factor, WRINKLED1, of Arabidopsis thaliana binds to the AW-box sequence conserved among proximal upstream regions of genes involved in fatty acid synthesis. The Plant Journal 60:476-487.
Mhaske, V., K. Beldjilali, J. Ohlrogge, and M. Pollard. 2005. Isolation and characterization of an Arabidopsis thaliana knockout line for phospholipid: diacylglycerol transacylase gene (At5g13640). Plant Physiol Biochem 43:413-417.
Mu, J.Y., H.L. Tan, Q. Zheng, F.Y. Fu, Y. Liang, J.A. Zhang, X.H. Yang, T. Wang, K. Chong, X.J. Wang, and J.R. Zuo. 2008. Leafy COTYLEDON1 is a key regulator of fatty acid biosynthesis in Arabidopsis. Plant Physiology 148:1042-1054.

Wang, H.-W., J.-S. Zhang, J.-Y. Gai, and S.-Y. Chen. 2006. Cloning and comparative analysis of the gene encoding diacylglycerol acyltransferase from wild type and cultivated soybean. Theoretical and Applied Genetics 112:1086-1097.
Wang, H.W., B. Zhang, Y.J. Hao, J. Huang, A.G. Tian, Y. Liao, J.S. Zhang, and S.Y. Chen. 2007a. The soybean Dof-type transcription factor genes, GmDof4 and GmDof11, enhance lipid content in the seeds of transgenic Arabidopsis plants. Plant Journal 52:716-729.
Wang, H.Y., J.H. Guo, K.N. Lambert, and Y. Lin. 2007b. Developmental control of Arabidopsis seed oil biosynthesis. Planta 226:773-783.
Ohlrogge, J.B., and J. Browse. 1995. Lipid biosynthesis. Plant Cell 7:957-970.
Rao, S., and D. Hildebrand. 2009. Changes in Oil Content of Transgenic Soybeans Expressing the Yeast SLC1 Gene. Lipids 44:945-951.
Routaboul, J.-M., C. Benning, N. Bechtold, M. Caboche, and L. Lepiniec. 1999. The TAG1 locus of Arabidopsis encodes for a diacylglycerol acyltransferase. Plant Physiology and Biochemistry 37:831-840.
Saha, S., B. Enugutti, S. Rajakumari, and R. Rajasekharan. 2006. Cytosolic Triacylglycerol Biosynthetic Pathway in Oilseeds. Molecular Cloning and Expression of Peanut Cytosolic Diacylglycerol Acyltransferase. Plant Physiology 141:1533-1543.
Yu, K., R. Li, T. Hatanaka and D. Hildebrand. 2008. Cloning and functional analysis of two type 1 diacylglycerol acyltransferases from Vernonia galamensis, Phytochemistry 69:1119-1127.
Schmutz, J., et al. 2010. Genome sequence of the palaeopolyploid soybean. Nature 463:178-183.
Shen, B., W.B. Allen, P. Zheng, C. Li, K. Glassman, J. Ranch, D. Nubel, and M.G. Tarczynski. 2010. Expression of ZmLEC1 and ZmWRI1 Increases Seed Oil Production in Maize. Plant Physiol.:pp. 110.157537.
Siloto, R.M.P., K. Findlay, A. Lopez-Villalobos, E.C. Yeung, C.L. Nykiforuk, and M.M. Moloney. 2006. The Accumulation of Oleosins Determines the Size of Seed Oilbodies in Arabidopsis. Plant Cell 18:1961-1974.
Zhang, F.-Y., M.-F. Yang, and Y.-N. Xu. 2005. Silencing of DGAT1 in tobacco causes a reduction in seed oil content. Plant science 169:689-694.
Ståhl, U., A. Carlsson, M. Lenman, A. Dahlqvist, B. Huang, W. Bana, A. Bana, and S. Stymne. 2004. Cloning and Functional Characterization of a Phospholipid:Diacylglycerol Acyltransferase from Arabidopsis Plant Physiol. 135:1324-1335.
Stobart, K., M. Mancha, M. Lenman, A. Dahlqvist, and S. S. 1997. Triacylglycerols are synthesised and utilized by transacylation reactions in microsomal preparations of developing safflower (Carthamus tinctorius L.) seeds. Planta 203:58-66.
Taylor, D.C., Z. Yan, A. Kumar, T. Francis, E.M. Giblin, D.L. Barton, J.R. Ferrie, A. Laroche, S. Shah, Z. Weiming, C.L. Snyder, L. Hall, G. Rakow, J.L. Harwood, and R.J. Weselake. 2009. Molecular modification of triacylglycerol accumulation by over-expression of DGAT1 to produce canola with increased seed oil content under field conditions. Botany 87:533-543.
Turkish, A.R., et al., 2005. Identification of Two Novel Human Acyl-CoA Wax Alcohol Acyltransferases: Members of the Diacylglycerol Acyltransferase 2 (DGAT2) Gene Superfamily. Journal of biological chemistry 280:14755-14764.
Tzen, J.T.C., Y.K. Lai, K.L. Chan, and A.H.C. Huang. 1990. Oleosin isoforms of high and low molecular weights are present in the oil bodies of diverse seed species. Plant-physiology 94:1282-1289.
Zhang, M., J. Fan, D.C. Taylor, and J.B. Ohlrogge. 2009. DGAT1 and PDAT1 Acyltransferases Have Overlapping Functions in Arabidopsis Triacylglycerol Biosynthesis and Are Essential for Normal Pollen and Seed Development. Plant Cell 21:3885-3901.
Egli, D.B. and D.M. Tekrony. Soybean seed germination, vigor and field emergence. 1995. Seed Sci. & Technol. 23, pp. 595-607.

\* cited by examiner

```
                             SEQUENCE LISTING

<160> NUMBER OF SEQ ID NOS: 19

<210> SEQ ID NO 1
<211> LENGTH: 1828
<212> TYPE: DNA
<213> ORGANISM: Vernonia galamensis

<400> SEQUENCE: 1
tctgagctca aatcaaattt ctgcgactca tacaggattc aactcaatac tttcttgatc       60
ggttctgctg ttcatttact tgtaatttct acttctgctt tgctttcatt tcaagctttt      120
ttccttaata atggcgttat tagatacgcc tcagattgga gaaataacga ccaccgccac      180
cacaactata agacggcgga ccactgtcaa gcctgatgct ggaatcggag atggattgtt      240
tgattcttcg tcgtcttcca aaaccaactc atccttcgag gatggtgaca gtttgaatgg      300
tgatttcaat gacaaattta aggaacagat cggagctggt gatgaatcca aggacgactc      360
```

```
caaggggaac ggacagaaga tagatcacgg aggagttaaa aagggacgtg aaacgactgt      420
ggtgcattat gcttatcggc cttcttctcc ggctcatcgg agaattaaag aatctccgct      480
tagctctgac gccatcttca agcagagtca tgcaggcctc tttaaccttt gcatagtggt      540
gcttgttgca gtaaatggta ggctcatcat tgagaatctg atgaagtatg gactattgat      600
caattccaac ttttggttca gttcgagatc attgagagac tggccacttc tgatgtgctg      660
cctcactcct tctgactttc cacttgctgc ctacattgtt gagaaattgg catggaaaaa      720
acgtatatcc gaccctgttg taatcacact ccatgttata ataactacaa ctgcaattct      780
ttatccggtc ttcatgattc tgaggttcga ttcagttgtt ctatcaggcg tctcgttgat      840
gctgtgtgct tgcattaatt ggttgaagtt ggtatctttt gtgcatacaa attatgacat      900
gcggtcgctt ttgaactcaa ctgataaggg agaagtggaa cccatgtctt caaatatgga      960
ttatttttat gatgtcaact tcaaaagctt ggtttatttc atggttgctc aactttgtg      1020
ttaccagata agctatcctc gcactgcatt tattcgaaag ggttgggtgt acggcaact      1080
gatcaagcta gtaatattta cagggttcat gggattcatc attgaacaat atatcaatcc      1140
gattgtcaaa aattctcgtc atccattgaa aggagacttt ttatatgcga ttgagcgggt      1200
tttaaagctt tcagttccga atttatatgt gtggctctgt atgttctact gcttttttca      1260
cctttggtta aatatacttg ctgagcttct ttgttttggg gatcgtgaat tttataaaga      1320
ttggtggaat gcacaaacta ttgaagagta ttggaggcta tggaatatgc ctgttcataa      1380
atggattgtt aggcaccttt attttccatg cttgcgtaat gggatacctc agggtgctgc      1440
catattggtt gcattttca tgtctgccgt gttccatgag ctttgtattg ctgttccctg      1500
ccacattttc aagttttggg cttttatcgg gatcatgttt caggtcccgt tggtcctact      1560
cacaaattac ttgcagcaca gtttcaaaa ctcgatggtg ggaaatatga tcttctggtg      1620
cttttttcagc attttggtc aacccatgtg tgtattactt tactaccatg atgtcatgaa      1680
tcaaaagggg aaaagcaaat aaaaagatgt gattgtgttg ctccatttga tctcatagca      1740
tgactggact aaacaaaccc aagggacaca ttttagtcct taaaggaaaa tttttgtagg      1800
aaaaaaaaaa aaaaaaaaaa aaaaaaaa                                        1828
```

<210> SEQ ID NO 2
<211> LENGTH: 523
<212> TYPE: PRT
<213> ORGANISM: Vernonia galamensis

<400> SEQUENCE: 2

```
Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
            20                  25                  30

Gly Asp Gly Leu Phe Asp Ser Ser Ser Ser Lys Thr Asn Ser Ser
        35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110
```

-continued

```
Lys Glu Ser Pro Leu Ser Ser Asp Ala Ile Phe Lys Gln Ser His Ala
            115                 120                 125
Gly Leu Phe Asn Leu Cys Ile Val Val Leu Val Ala Val Asn Gly Arg
130                 135                 140
Leu Ile Ile Glu Asn Leu Met Lys Tyr Gly Leu Leu Ile Asn Ser Asn
145                 150                 155                 160
Phe Trp Phe Ser Ser Arg Ser Leu Arg Asp Trp Pro Leu Leu Met Cys
                165                 170                 175
Cys Leu Thr Pro Ser Asp Phe Pro Leu Ala Ala Tyr Ile Val Glu Lys
            180                 185                 190
Leu Ala Trp Lys Lys Arg Ile Ser Asp Pro Val Val Ile Thr Leu His
            195                 200                 205
Val Ile Ile Thr Thr Thr Ala Ile Leu Tyr Pro Val Phe Met Ile Leu
            210                 215                 220
Arg Phe Asp Ser Val Val Leu Ser Gly Val Ser Leu Met Leu Cys Ala
225                 230                 235                 240
Cys Ile Asn Trp Leu Lys Leu Val Ser Phe Val His Thr Asn Tyr Asp
                245                 250                 255
Met Arg Ser Leu Leu Asn Ser Thr Asp Lys Gly Glu Val Glu Pro Met
                260                 265                 270
Ser Ser Asn Met Asp Tyr Phe Tyr Asp Val Asn Phe Lys Ser Leu Val
            275                 280                 285
Tyr Phe Met Val Ala Pro Thr Leu Cys Tyr Gln Ile Ser Tyr Pro Arg
            290                 295                 300
Thr Ala Phe Ile Arg Lys Gly Trp Val Leu Arg Gln Leu Ile Lys Leu
305                 310                 315                 320
Val Ile Phe Thr Gly Phe Met Gly Phe Ile Ile Glu Gln Tyr Ile Asn
                325                 330                 335
Pro Ile Val Lys Asn Ser Arg His Pro Leu Lys Gly Asp Phe Leu Tyr
                340                 345                 350
Ala Ile Glu Arg Val Leu Lys Leu Ser Val Pro Asn Leu Tyr Val Trp
            355                 360                 365
Leu Cys Met Phe Tyr Cys Phe Phe His Leu Trp Leu Asn Ile Leu Ala
            370                 375                 380
Glu Leu Leu Cys Phe Gly Asp Arg Glu Phe Tyr Lys Asp Trp Trp Asn
385                 390                 395                 400
Ala Gln Thr Ile Glu Glu Tyr Trp Arg Leu Trp Asn Met Pro Val His
                405                 410                 415
Lys Trp Ile Val Arg His Leu Tyr Phe Pro Cys Leu Arg Asn Gly Ile
                420                 425                 430
Pro Lys Gly Ala Ala Ile Leu Val Ala Phe Phe Met Ser Ala Val Phe
            435                 440                 445
His Glu Leu Cys Ile Ala Val Pro Cys His Ile Phe Lys Phe Trp Ala
            450                 455                 460
Phe Ile Gly Ile Met Phe Gln Val Pro Leu Val Leu Leu Thr Asn Tyr
465                 470                 475                 480
Leu Gln His Lys Phe Gln Asn Ser Met Val Gly Asn Met Ile Phe Trp
                485                 490                 495
Cys Phe Phe Ser Ile Phe Gly Gln Pro Met Cys Val Leu Leu Tyr Tyr
            500                 505                 510
His Asp Val Met Asn Gln Lys Gly Lys Ser Lys
            515                 520
```

```
<210> SEQ ID NO 3
<211> LENGTH: 1738
<212> TYPE: DNA
<213> ORGANISM: Vernonia galamensis

<400> SEQUENCE: 3
gttcgtaatt cggctgtggt ttcctttcca acatttctac gtaatcatgg cgttgttaga      60
tacgcctcaa attggagaaa taacgacgac cgcaacaacg accattaggc agcaccccct     120
gggcaagcct gatgctggaa ttggagatgg attgttttct tcgtcgtctt ccaaaaccaa     180
ctcatccttc gaggatggtg acagtttgaa tggtgatttc aatgacaaat ttaaggaaca     240
gatcggagct ggtgatgaat ccaagaaggg gaacggaaag atagatcacg gaggagttaa     300
aaagggacgt gaaacgactg tggtgcatta tgcttatcgg ccttcttctc cggctcatcg     360
gagaattaaa gaatctccgc ttagctctga cgccatcttc aagcagagtc atgcaggcct     420
ctttaacctt tgcatagtgg tgcttgttgc agtaaatggt aggctcatca tcgagaatct     480
gatgaagtat ggactattga ttaattccaa attttggttc agttcgagat cattgagaga     540
ctggccgctt ctgatgtgtt ggctgacccc ctccgacttc cccctcgccg cctacattgt     600
cgagaaattg gcatggaaaa aacgtatatc cgaccctgtt gtaatcacac tccatgttgt     660
aataactaca actgcaattc tctatccgat cttcatgatt ctgaggttcg actcggtcgt     720
tctattaggc gtctcgttga tgctgtgtgc ttgcattaat tggttgaagt tggtatcttt     780
tgtgcataca aattatgaca tgcggtcgct attgaactca actggtaagg gagaagtgga     840
gcccatgtct tcaaatatgg actactttta tgatatcaac ttcaaaagct tggtttattt     900
catggttgct ccaactttgt gttaccagat aagctatcct cgcaccgcct ttattcgaaa     960
gggctgggtg ttccggcaac tgatcaagct agtaatattt acagggttca tgggattcat    1020
cattgaacaa tatatcaatc cgattgtcaa aaattctcgg catccattga acggagactt    1080
tttatatgcg attgaacgag tattaaaggt ttcagttccg aatttatatg tgtggctctg    1140
tatgttctat tgctttttc accttggtt aaatatactt gctgagcttc tttggtttgg    1200
ggatcgtgaa ttttataaag attggtggaa tacacaaact attgaagagt attggaggct    1260
atggaatatg cctgttcata agtggattgt taggcacctc tattttccat gcttgcgtaa    1320
tgggatatct aagggtgctg ccatattggt tgcttttttc atgtctgccg tgttccacga    1380
gctttgcata gctgttccct gccacatttt aaagttttgg gctttcatcg ggatcatgtt    1440
ccaggtcccg ttggtactac tcacaaatta cttgcagcac aagtttcaaa actcgatggt    1500
gggaaacatg atcttttggt gcttcttcag cattttcggt caacccatgt gtgtatttct    1560
ttactaccat gaagtcaatc aaaaggggaa aagcaaatga aaggacgtta tcgtatttcc    1620
ccaatctttc ttatatcgtg aatctaatat ccataacaaa gcaaacaat taagtcactg    1680 gagaatacta ttagcaggta ataaagaacc aaacaaaaaa aaaaaaaaa aaaaaaaa      1738

<210> SEQ ID NO 4
<211> LENGTH: 517
<212> TYPE: PRT
<213> ORGANISM: Vernonia galamensis

<400> SEQUENCE: 4

Met Ala Leu Leu As

Gly Asp Gly Leu Phe Ser Ser Ser Ser Lys Thr Asn Ser Ser Phe
    35                  40                  45

Glu Asp Gly Asp Ser Leu Asn Gly Asp Phe Asn Asp Lys Phe Lys Glu
50                  55                  60

Gln Ile Gly Ala Gly Asp Glu Ser Lys Lys Gly Asn Gly Lys Ile Asp
65                  70                  75                  80

His Gly Gly Val Lys Lys Gly Arg Glu Thr Thr Val Val His Tyr Ala
                85                  90                  95

Tyr Arg Pro Ser Ser Pro Ala His Arg Arg Ile Lys Glu Ser Pro Leu
            100                 105                 110

Ser Ser Asp Ala Ile Phe Lys Gln Ser His Ala Gly Leu Phe Asn Leu
            115                 120                 125

Cys Ile Val Val Leu Val Ala Val Asn Gly Arg Leu Ile Ile Glu Asn
    130                 135                 140

Leu Met Lys Tyr Gly Leu Leu Ile Asn Ser Lys Phe Trp Phe Ser Ser
145                 150                 155                 160

Arg Ser Leu Arg Asp Trp Pro Leu Leu Met Cys Trp Leu Thr Pro Ser
                165                 170                 175

Asp Phe Pro Leu Ala Ala Tyr Ile Val Glu Lys Leu Ala Trp Lys Lys
            180                 185                 190

Arg Ile Ser Asp Pro Val Val Ile Thr Leu His Val Ile Thr Thr
            195                 200                 205

Thr Ala Ile Leu Tyr Pro Ile Phe Met Ile Leu Arg Phe Asp Ser Val
    210                 215                 220

Val Leu Leu Gly Val Ser Leu Met Leu Cys Ala Cys Ile Asn Trp Leu
225                 230                 235                 240

Lys Leu Val Ser Phe Val His Thr Asn Tyr Asp Met Arg Ser Leu Leu
                245                 250                 255

Asn Ser Thr Gly Lys Gly Glu Val Glu Pro Met Ser Ser Asn Met Asp
            260                 265                 270

Tyr Phe Tyr Asp Ile Asn Phe Lys Ser Leu Val Tyr Phe Met Val Ala
            275                 280                 285

Pro Thr Leu Cys Tyr Gln Ile Ser Tyr Pro Arg Thr Ala Phe Ile Arg
    290                 295                 300

Lys Gly Trp Val Phe Arg Gln Leu Ile Lys Leu Val Ile Phe Thr Gly
305                 310                 315                 320

Phe Met Gly Phe Ile Ile Glu Gln Tyr Ile Asn Pro Ile Val Lys Asn
                325                 330                 335

Ser Arg His Pro Leu Asn Gly Asp Phe Leu Tyr Ala Ile Glu Arg Val
            340                 345                 350

Leu Lys Val Ser Val Pro Asn Leu Tyr Val Trp Leu Cys Met Phe Tyr
            355                 360                 365

Cys Phe Phe His Leu Trp Leu Asn Ile Leu Ala Glu Leu Leu Trp Phe
    370                 375                 380

Gly Asp Arg Glu Phe Tyr Lys Asp Trp Asn Thr Gln Thr Ile Glu
385                 390                 395                 400

Glu Tyr Trp Arg Leu Trp Asn Met Pro Val His Lys Trp Ile Val Arg
                405                 410                 415

His Leu Tyr Phe Pro Cys Leu Arg Asn Gly Ile Ser Lys Gly Ala Ala
            420                 425                 430

Ile Leu Val Ala Phe Phe Met Ser Ala Val Phe His Glu Leu Cys Ile
            435                 440                 445

Ala Val Pro Cys His Ile Leu Lys Phe Trp Ala Phe Ile Gly Ile Met

```
                    450               455               460
Phe Gln Val Pro Leu Val Leu Leu Thr Asn Tyr Leu Gln His Lys Phe
465                 470               475               480

Gln Asn Ser Met Val Gly Asn Met Ile Phe Trp Cys Phe Phe Ser Ile
                485               490               495

Phe Gly Gln Pro Met Cys Val Phe Leu Tyr Tyr His Glu Val Asn Gln
                500               505               510

Lys Gly Lys Ser Lys
        515

<210> SEQ ID NO 5
<211> LENGTH: 1017
<212> TYPE: DNA
<213> ORGANISM: Vernonia galamensis

<400> SEQUENCE: 5
atgggtgaat tgctaatca  taacagaatt  aatagtaacg  atgttaaaaa  cgaggaaaag    60
ggcaacagcc gtgtcttcaa tggacgagaa  atctatcaca  ctagtatccc  tcgggcatta   120
atagcattga gtttgtggat agggagtata  cactttatat  tgttcttgtt  attcatcagt   180
tatatcttgt tcagtcctcc cacgagcgct  atggttatcg  gatttcaggt  aattctgatg   240
gtactaccac tcgatgaaaa tagtaaattc  ggcctccgaa  tctttagtta  tgtcagtaaa   300
tacgttatgg acattttcc  cgttaccctc  tatgtagagg  atatgaaatg  cttccaaagc   360
aaccgagcct atgtgtttgg gttccatcct  catagtgtct  tcccgctggg  tgttgctatc   420
ctttgcgaac acctggctgt gatcccaatt  cccaatatca  agttcctgac  cagtaaccct   480
atcttcagaa ctcctgttct gaggcagatt  tggagttggt  gcggtgctat  tgccgctagc   540
aaaaagaact tcacggctta ctcagcgca   ggttacactt  gcgttgtgat  tcccggtgga   600
gttcaggaga ttctccatat gagacagggt  gctgagagtg  ataacgtctt  tatcagcagg   660
agaaagggct ttatcaaggt cgctatacag  acggtaaccc  cgctagtacc  tgtcttcttt   720
ttcggacagg ctcatacgta caagtggtgg  agacccaagt  gcgaattcta  cgtactgaag   780
gctagggcta ttaggttcgg acctaccgta  ttctggggaa  ggctcggaag  ccatctgcca   840
tgtaagaatc ccacggttgt cgtagtgggt  agacctatca  ctgtagagaa  aacgctcaag   900
cctacgatcg atgagatcag caagttccag  agagagtaca  cggtcagtct  aaggaatctc   960
ttcgacaaat acaagacgga gatcggtcac  cctggtctgg  agttgaagat  cttgtga     1017

<210> SEQ ID NO 6
<211> LENGTH: 338
<212> TYPE: PRT
<213> ORGANISM: Vernonia galamensis

<400> SEQUENCE: 6

Met Gly Glu Phe Ala Asn His Asn Arg Ile Asn Ser Asn Asp Val Lys
1               5                   10                  15

Asn Glu Glu Lys Gly Asn Ser Arg Val Phe Asn Gly Arg Glu Ile Tyr
            20                  25                  30

His Thr Ser Ile Pro Arg Ala Leu Ile Ala Leu Ser Leu Trp Ile Gly
        35                  40                  45

Ser Ile His Phe Ile Leu Phe Leu Leu Phe Ile Ser Tyr Ile Leu Phe
    50                  55                  60

Ser Pro Pro Thr Ser Ala Met Val Ile Gly Phe Gln Val Ile Leu Met
65                  70                  75                  80
```

-continued

```
Val Leu Pro Leu Asp Glu Asn Ser Lys Phe Gly Leu Arg Ile Phe Ser
                 85                  90                  95
Tyr Val Ser Lys Tyr Val Met Gly His Phe Pro Val Thr Leu Tyr Val
            100                 105                 110
Glu Asp Met Lys Cys Phe Gln Ser Asn Arg Ala Tyr Val Phe Gly Phe
        115                 120                 125
His Pro His Ser Val Phe Pro Leu Gly Val Ala Ile Leu Cys Glu His
    130                 135                 140
Leu Ala Val Ile Pro Ile Pro Asn Ile Lys Phe Leu Thr Ser Asn Pro
145                 150                 155                 160
Ile Phe Arg Thr Pro Val Leu Arg Gln Ile Trp Ser Trp Cys Gly Ala
                165                 170                 175
Ile Ala Ala Ser Lys Lys Asn Phe Thr Ala Tyr Leu Ser Ala Gly Tyr
            180                 185                 190
Thr Cys Val Val Ile Pro Gly Gly Val Gln Glu Ile Leu His Met Arg
        195                 200                 205
Gln Gly Ala Glu Ser Asp Asn Val Phe Ile Ser Arg Arg Lys Gly Phe
    210                 215                 220
Ile Lys Val Ala Ile Gln Thr Val Thr Pro Leu Val Pro Val Phe Phe
225                 230                 235                 240
Phe Gly Gln Ala His Thr Tyr Lys Trp Trp Arg Pro Lys Cys Glu Phe
                245                 250                 255
Tyr Val Leu Lys Ala Arg Ala Ile Arg Phe Gly Pro Thr Val Phe Trp
            260                 265                 270
Gly Arg Leu Gly Ser His Leu Pro Cys Lys Asn Pro Thr Val Val Val
        275                 280                 285
Val Gly Arg Pro Ile Thr Val Glu Lys Thr Leu Lys Pro Thr Ile Asp
    290                 295                 300
Glu Ile Ser Lys Phe Gln Arg Glu Tyr Thr Val Ser Leu Arg Asn Leu
305                 310                 315                 320
Phe Asp Lys Tyr Lys Thr Glu Ile Gly His Pro Gly Leu Glu Leu Lys
                325                 330                 335
Ile Leu

<210> SEQ ID NO 7
<211> LENGTH: 22
<212> TYPE: DNA
<213> ORGANISM: Artificial Sequence
<220> FEATURE:
<223> OTHER INFORMATION: Forward Primer
<220> FEATURE:
<221> NAME/KEY: misc_feature
<222> LOCATION: (6)..(6)
<223> OTHER INFORMATION: y is equal to any pyrimidine
<220> FEATURE:
<221> NAME/KEY: misc_feature
<222> LOCATION: (9)..(9)
<223> OTHER INFORMATION: w is equal to adenine or thymine or uracil
<220> FEATURE:
<221> NAME/KEY: misc_feature
<222> LOCATION: (19)..(19)
<223> OTHER INFORMATION: s is equal to guanine or cytosine
<220> FEATURE:
<221> NAME/KEY: misc_feature
<222> LOCATION: (21)..(21)
<223> OTHER INFORMATION: r is equal to any purine

<400> SEQUENCE: 7
gctccyacwt tgtgttatsa rc                                           22
```

```
<210> SEQ ID NO 8
<211> LENGTH: 24
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<222> LOCATION: (4)..(4)
<223> OTHER INFORMATION: y is equal to any pyrimidine
<220> FEATURE:
<221> NAME/KEY: misc_feature
<222> LOCATION: (7)..(7)
<223> OTHER INFORMATION: r is equal to any purine
<220> FEATURE:
<221> NAME/KEY: misc_feature
<222> LOCATION: (10)..(10)
<223> OTHER INFORMATION: r is equal to any purine
<220> FEATURE:
<221> NAME/KEY: misc_feature
<222> LOCATION: (13)..(13)
<223> OTHER INFORMATION: r is equal to any purine
<220> FEATURE:
<221> NAME/KEY: misc_feature
<222> LOCATION: (16)..(16)
<223> OTHER INFORMATION: s is equal to guanine or cytosine

<400> SEQUENCE: 8
ccayttrtgr acrggsatat tcca                                          24

<210> SEQ ID NO 9
<211> LENGTH: 7
<212> TYPE: PRT
<213> ORGANISM: Artificial Sequence
<220> FEATURE:
<223> OTHER INFORMATION: Conserved Amino Acid Sequence of Diacyghlycerol
      Acyltransferases from Arabidopsis Thaliana and Mus Musculus
<220> FEATURE:
<221> NAME/KEY: MOD_RES
<222> LOCATION: (7)..(7)
<223> OTHER INFORMATION: X is equal to glutamic acid or glutamine

<400> SEQUENCE: 9

Ala Pro Thr Leu Cys Tyr Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Conserved Amino Acid Sequence of Diacylglycerol
      Acyltransferases from Arabidopsis Thaliana and Mus Musculus
<220> FEATURE:
<221> NAME/KEY: MOD_RES
<222> LOCATION: (3)..(3)
<223> OTHER INFORMATION: X is equal to isoleucine or methionine

<400> SEQUENCE: 10

Trp Asn Xaa Pro Val His Lys Trp
1               5

<210> SEQ ID NO 11
<211> LENGTH: 28
<212> TYPE: DNA
<213> ORGANISM: Artificial Sequence
<220> FEATURE:
<223> OTHER INFORMATION: VgDGAT2 Forward Primer

<400> SEQUENCE: 11
tcgaaagggt tgggtgttac ggcaactg                                      28
```

<210> SEQ ID NO 12
<211> LENGTH: 28
<212> TYPE: DNA
<213> ORGANISM: Artificial Sequence
<220> FEATURE:
<223> OTHER INFORMATION: VgDGAT Reverse Primer

<400> SEQUENCE: 12
cagttgccgt aacacccaac cctttcga                                28

<210> SEQ ID NO 13
<211> LENGTH: 26
<212> TYPE: DNA
<213> ORGANISM: Artificial Sequence
<220> FEATURE:
<223> OTHER INFORMATION: Euphorbia Forward Primer

<400> SEQUENCE: 13
caacttgaca aactgacgga acaccc                                  26

<210> SEQ ID NO 14
<211> LENGTH: 26
<212> TYPE: DNA
<213> ORGANISM: Artificial Sequence
<220> FEATURE:
<223> OTHER INFORMATION: Euphorbia Reverse Primer

<400> SEQUENCE: 14
gggtgttccg tcagtttgtc aagttg                                  26

<210> SEQ ID NO 15
<211> LENGTH: 30
<212> TYPE: DNA
<213> ORGANISM: Artificial Sequence
<220> FEATURE:
<223> OTHER INFORMATION: Glycine Max Forward Primer 1

<400> SEQUENCE: 15
gcgtaaagaa ggtttccctt gagaggatgc                              30

<210> SEQ ID NO 16
<211> LENGTH: 30
<212> TYPE: DNA
<213> ORGANISM: Artificial Sequence
<220> FEATURE:
<223> OTHER INFORMATION: Glycine max Reverse Primer 1

<400> SEQUENCE: 16 gttgcccta cattatgtta ccagccaagc                               30

<210> SEQ ID NO 17
<211> LENGTH: 22
<212> TYPE: DNA
<213> ORGANISM: Artificial Sequence
<220> FEATURE:
<223> OTHER INFORMATION: Glycine max Forward Primer 2

<400> SEQUENCE: 17
gaaaacacgc tcggtcttct tc                                      22

<210> SEQ ID NO 18
<211> LENGTH: 22
<212> TYPE: DNA
<213> ORGANISM: Artificial Sequence
<220> FEATURE:
<223> OTHER INFORMATION: Glycine max Reverse Primer 2

-continued

```
<400> SEQUENCE: 18
tacaattgcc agaggagagt tg                                              22

<210> SEQ ID NO 19
<211> LENGTH: 1344
<212> TYPE: DNA
<213> ORGANISM: Stokesia laevis

<400> SEQUENCE: 19
gagaagttga ccataaatca tttatcaaca tgggtgccgg cggtcgtggt cggacatcgg     60
aaaaatcggt catggaacgt gtctcagttg atccagtaac cttctcactg agtgaattga    120
agcaagcaat ccctccccat tgcttccaga gatctgtaat ccgctcatct tactatgttg    180
ttcaagatct cattattgcc tacatcttct acttccttgc caacacatat atccctactc    240
ttcctactag tctagcctac ttagcttggc ccgtttactg gttctgtcaa gctagcgtcc    300
tcactggctt atggatcctc ggccacgaat gtggtcacca tgcctttagc aactacacat    360
ggtttgacga cactgtgggc ttcatcctcc actcatttct cctcaccccg tatttctctt    420
ggaaattcag tcaccggaat caccattcca acacaagttc gattgataac gatgaagttt    480
acattccgaa aagcaagtcc aaactcgcgc gtatctataa acttcttaac aacccacctg    540
gtcggctgtt ggttttgatt atcatgttca ccctaggatt tccttttatac ctcttgacaa    600 atatttccgg caagaaatac gacaggtttg ccaaccactt cgaccccatg agtccaattt    660
tcaaagaacg tgagcggttt caggtcttcc tttcggatct tggtcttctt gccgtgtttt    720
atggaattaa agttgctgta gcaaataaag gagctgcttg ggtagcgtgc atgtatggag    780
ttccggtatt aggcgtattt acctttttcg atgtgatcac cttcttgcac cacacccatc    840
agtcgtcgcc tcattatgat tcaactgaat ggaactggat cagaggggcc ttgtcagcaa    900
tcgataggga ctttggattc ctgaatagtg ttttccatga tgttacacac actcatgtca    960
tgcatcattt gttttcatac attccacact atcatgcaaa ggaggcaagg gatgcaatca   1020
agccaatctt gggcgacttt tatatgatcg acaggactcc aattttaaaa gcaatgtgga   1080
gagagggcag ggagtgcatg tacatcgagc ctgatagcaa gctcaaaggt gtttattggt   1140
atcataaatt gtgatcatat gcaaaatgca catgcattt caaaccctct agttacgttt   1200
gttctatgta taataaaccg ccggtccttt ggttgactat gcctaagcca ggcgaaacag   1260
ttaaataata tcggtatgat gtgtaatgaa agtatgtggt tgtctggttt tgttgctatg   1320
aaagaaagta tgtggttgtc ggtc                                         1344
```

METHODS FOR INCREASING RENEWABLE OIL PRODUCTION

RELATED APPLICATIONS

This application claims priority from U.S. Provisional Application Ser. No. 61/371,936, filed Aug. 9, 2010, the entire disclosure of which is incorporated herein by this reference.

TECHNICAL FIELD

The presently-disclosed subject matter relates to methods for increasing renewable oil production. In particular, the presently-disclosed subject matter relates to methods for increasing renewable oil production in a plant, where the expression of a *Vernonia galamensis* diacylglycerol acyltransferase (VgDGAT) polypeptide increases an amount of renewable oil in the plant.

BACKGROUND

Global plant oil production exceeded 120 metric tons (MT) in 2009, and continues to be dominated by four main oil crops: palm, soybeans, rapeseed or canola, and sunflowers (Wilson and Hildebrand, 2010). Indeed, world-wide palm and soybean production has increased rapidly in recent years, with rapeseed also showing steady increases, and it is expected that this trend will only continue as the projected global oil production in 2010 was expected to climb to over 170 million MT.

Of the oil being produced from the four main oil crops, palm oil production has been dominated by Malaysia and Indonesia, while the vast majority of soybeans are produced in the United States, Brazil, China and Argentina. Despite the production of different oils by different countries, however, global oilseed production has been consistently dominated by soybeans and has been followed by rapeseed as a distant second (Wilson and Hildebrand, 2010). Over 200 million MT of soybean seeds have been produced in recent years, and this dominance is believed to be because, among oilseeds, soybeans are low in oil and high in protein making soybeans the dominant global protein source. On average, soybeans consist of approximately 20% oil and 40% protein on a dry weight basis, whereas rapeseed is approximately 50% oil and palm fruit is close to 90% oil and includes both palm fruit oil and kernel oil.

Breeding for increased oilseed yield per unit land area has also continued to progress in recent years with steady soybean yield increases being a good example (Egli, 2008a; Egli, 2008b). This increased yield is often with little or no increased inputs, thus making renewable oil production from plants less expensive over time and, at the same time, more competitive with petroleum as an industrial chemical feedstock. Indeed, while most plant oil continues to be produced and used for food purposes, an increasing proportion of plant oil is being utilized for industrial uses, with the proportion of industrial versus food usage having increased from approximately 10% to approximately 20% in the last 10 years.

Because U.S. and global seed and oil production is extensive and important for the both the production of oils for human and animal consumption and for industrial purposes, the value of even a 3-5% increase in seed oil content is also significant and has been increasingly recognized. Accordingly, a method of increasing oil content by only a small percentage would be both desirable and beneficial. More specifically, a method of increasing renewable oil production in a plant that is not accompanied by a concomitant decrease in protein levels in the plant, would be highly desirable and beneficial not only for purposes of human consumption, but also from an industrial perspective.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods of increasing renewable oil production and, in particular, methods of increasing renewable oil production in a plant. In some embodiments, a method of increasing renewable oil production in a plant is provided that comprises transforming a plant cell with an isolated nucleic acid encoding a *Vernonia galamensis* diacylglycerol acyltransferase 1 (VgDGAT1) polypeptide, wherein expression of the VgDGAT1 polypeptide increases an amount of renewable oil in the plant. In some embodiments, expression of the VgDGAT1 polypeptide increases the amount of renewable oil in the plant by at least about 2 or about 3 percent as compared to an amount of renewable oil in a control plant. In other embodiments, expression of the VgDGAT1 polypeptide increases the amount of renewable oil in the plant by at least about 5 percent as compared to an amount of renewable oil in a control plant.

In some embodiments of the methods for increasing renewable oil production in a plant, the plant is selected from: *Arachis hypogaea, Borago officinalis, Brassica campestris, Brassica napus, Brassica rapa, Camelina saliva, Cannabis saliva, Carthamus tinctorius, Cocos nucifera, Crambe abyssinica, Cuphea* species, *Glycine max, Gossypium hirsutum, Gossypium barbadense, Gossypium herbaceum, Helianthus annuus, Linum usitatissimum, Oenothera biennis, Olea europaea, Oryza sativa, Perilla frutescens, Ricinus communis, Salvia hispanica, Sesamum indicum, Sinapis alba, Theobroma cacao, Triticum* species, *Zea mays, Juglans* species, or *Prunis dulcis*. In some embodiments, increasing the amount of renewable oil in the plant comprises increasing the amount of renewable oil in a seed of the plant. In some embodiments, increasing the amount of renewable oil in the plant comprises increasing the amount of triacylglycerol (TAG) in the plant. In some embodiments, even though the amount of renewable oil found in the plant is increased, the protein levels in the plant are substantially unchanged as compared to a control plant. In some embodiments, both the amounts of renewable oil found in the plant and the amounts of protein found in the plant are increased.

In some embodiments of the presently-disclosed subject matter, the VgDGAT1 polypeptide expressed in the plant is a VgDGAT1a polypeptide. In some embodiments, the VgDGAT1a polypeptide is encoded by a nucleic acid molecule having the sequence of SEQ ID NO: 1. In some embodiments, the VgDGAT1a polypeptide comprises the amino acid sequence of SEQ ID NO: 2.

In other embodiments of the methods described herein, the VgDGAT1 polypeptide that is expressed in the plant is a VgDGAT1b polypeptide. In some of these embodiments, the VgDGAT1b polypeptide is encoded by a nucleic acid molecule having the sequence of SEQ ID NO: 3. In some embodiments, the VgDGAT1b polypeptide comprises the amino acid sequence of SEQ ID NO: 4.

In some embodiments of the presently-disclosed methods for increasing renewable oil production, the methods include the further step of transforming a plant cell with an isolated nucleic acid encoding a *Vernonia galamensis* diacylglycerol acyltransferase 2 (VgDGAT2) polypeptide, where the expression of the VgDGAT1 polypeptide and the VgDGAT2 polypeptide increases an amount of renewable oil in the plant. In some embodiments, the co-expression of the VgDGAT1 polypeptide and the VgDGAT2 polypeptide increases the amount of renewable oil in the plant in a synergistic manner. In some embodiments, the VgDGAT2 polypeptide is encoded by a nucleic acid molecule having the sequence of SEQ ID NO: 5. In some embodiments, the VgDGAT2 polypeptide comprises the amino acid sequence of SEQ ID NO: 6.

Further provided, in some embodiments of the presently-disclosed subject matter are methods of producing triacylglycerols (TAGs). In some embodiments, a method of producing a triacylglycerol (TAG) is provided that comprises transforming a cell with an isolated nucleic acid that encodes a *Vernonia galamensis* diacylglycerol acyltransferase 1 (VgDGAT1) polypeptide, wherein expression of the VgDGAT1 polypeptide increases an amount of TAG in the cell. In some embodiments, the cell is an animal cell, a plant cell, an algal cell, a fungal cell, or a yeast cell.

Still further provided, in some embodiments of the presently-disclosed subject matter, are methods for increasing renewable oil production in a plant that include transforming a plant cell with a first isolated nucleic acid encoding a *Vernonia galamensis* diacylglycerol acyltransferase (VgDGAT) polypeptide and a second isolated nucleic acid encoding an epoxygenase polypeptide, where the expression of the VgDGAT polypeptide and the epoxygenase polypeptide increases an amount of renewable oil in the plant. In some embodiments, the VgDGAT polypeptide is a VgDGAT1a polypeptide, a VgDGAT1b polypeptide, or a VgDGAT2 polypeptide. In some embodiments, the epoxygenase polypeptide is encoded by a nucleic acid sequence comprising the sequence of SEQ ID NO: 19.

In yet further embodiments of the presently-disclosed subject matter are transgenic plant cells capable of producing an increased amount of renewable oil. In some embodiments, a transgenic plant cell is provided that comprises an isolated nucleic acid encoding a *Vernonia galamensis* diacylglycerol acyltransferase 1 (VgDGAT1) polypeptide, wherein expression of the VgDGAT1 polypeptide increases an amount of renewable oil in the plant cell. In certain embodiments, the transgenic plant cell is operably linked to an expression control sequence. In some embodiments, the expression control sequence comprises a constitutive promoter or a seed-specific promoter.

Further features and advantages of the presently-disclosed subject matter will become evident to those of ordinary skill in the art after a study of the description, figures, and non-limiting examples in this document.

BRIEF DESCRIPTION OF THE SEQUENCE LISTING

Figure 1:
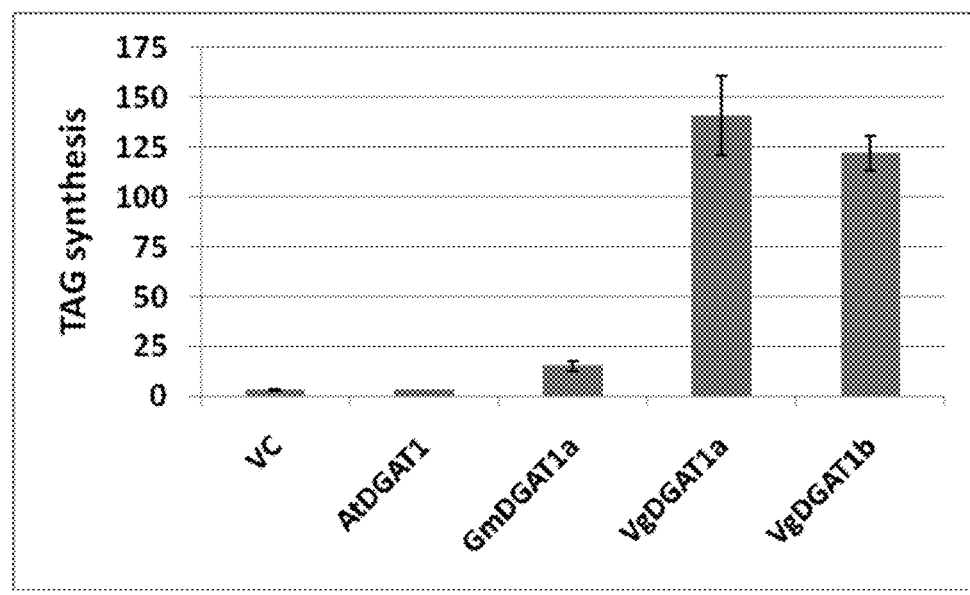
FIG. 1 is a graph showing the extent of TAG biosynthetic activity in yeast cells transfected with either a vector alone (VC), or a vector encoding an *Arabidopsis thaliana* DGAT1 polypeptide (AtDGAT1), a *Glycine max* DGAT1a polypeptide (GmDGAT1a), a *Vernonia galamensis* DGAT1a polypeptide (VgDGAT1a), or a *Vernonia galamensis* DGAT1b polypeptide (VgDGAT1b)

SEQ ID NO: 1 is a nucleic acid sequence of a diacylglycerol acyltransferase 1a cDNA obtained from *Vernonia galamensis*;

SEQ ID NO: 2 is an amino acid sequence of a diacylglycerol acyltransferase 1a polypeptide from *Vernonia galamensis*;

SEQ ID NO: 3 is a nucleic acid sequence of a diacylglycerol acyltransferase 1b cDNA obtained from *Vernonia galamensis*;

SEQ ID NO: 4 is an amino acid sequence of a diacylglycerol acyltransferase 1b polypeptide from *Vernonia galamensis*;

SEQ ID NO: 5 is a nucleic acid sequence of a diacylglycerol acyltransferase 2 cDNA obtained from *Vernonia galamensis*; and SEQ ID NO: 6 is an amino acid sequence of a diacylglycerol acyltransferase 2 polypeptide from *Vernonia galamensis*.

SEQ ID NO: 7 is a nucleic acid sequence of a degenerate forward primer for amplifying diacylglycerol acyltransferase cDNA;

SEQ ID NO: 8 is a nucleic acid sequence of a degenerate reverse primer for amplifying diacylglycerol acyltransferase cDNA;

SEQ ID NO: 9 is an amino acid sequence of a conserved region in diacylglycerol acyltransferases from *Arabidopsis thaliana* and *Mus musculus*;

SEQ ID NO: 10 is another amino acid sequence of a conserved region in diacylglycerol acyltransferases from *Arabidopsis thaliana* and *Mus musculus*;

SEQ ID NO: 11 is a nucleic acid sequence of a forward primer for amplifying *Vernonia galamensis* diacylglycerol acyltransferase cDNA;

SEQ ID NO: 12 is a nucleic acid sequence of a reverse primer for amplifying *Vernonia galamensis* diacylglycerol acyltransferase cDNA;

SEQ ID NO: 13 is a nucleic acid sequence of a forward primer for amplifying *Euphorbia lagascae* diacylglycerol acyltransferase cDNA;

SEQ ID NO: 14 is a nucleic acid sequence of a reverse primer for amplifying *Euphorbia lagascae* diacylglycerol acyltransferase cDNA;

SEQ ID NO: 15 is a nucleic acid sequence of a forward primer for amplifying *Glycine max* diacylglycerol acyltransferase cDNA;

SEQ ID NO: 16 is a nucleic acid sequence of a reverse primer for amplifying *Glycine max* diacylglycerol acyltransferase cDNA;

SEQ ID NO: 17 is a nucleic acid sequence of another forward primer for amplifying *Glycine max* diacylglycerol acyltransferase cDNA;

SEQ ID NO: 18 is a nucleic acid sequence of another reverse primer for amplifying *Glycine max* diacylglycerol acyltransferase cDNA; and SEQ ID NO: 19 is a nucleic acid sequence of an epoxygenase cDNA obtained from *Stokesia laevis*.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the following terms are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. In this regard, in some embodiments of the presently-disclosed subject matter, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Plant seed oils represent a significant renewable resource, with most plant seed oils being predominately composed of triacylglycerols (TAGs) that are produced via the sequential incorporation of fatty acids. In plants, this sequential incorporation of fatty acids into TAG is commonly known as the Kennedy pathway, which consists of three successive acylation reactions of the hydroxyl groups of glycerol by three acyl-CoA-dependent acyltransferases, starting from glycerol-3-phosphate (G3P). Specifically, in the Kennedy pathway, lysophosphatidic acid (LPA) and phosphatidic acid (PA) are first formed through two acylations catalyzed by the acyltransferases glycerol-3-phosphate (GPAT) and lyso-phosphatidic acid acyltransferase (LPAAT). PA is then dephosphorylated by the action of phosphatidate phosphatase (PAP) to form sn-1,2-diacylglycerol (sn-1,2 DAG). The final acylation of sn-1,2 DAG is the transfer of a fatty acyl moiety, such as from acyl-CoA, to the sn-3 position of diacylglycerol by diacylglycerol acyltransferase (DGAT) to generate TAG.

It is thought that DGAT is one of the rate-limiting steps in plant storage lipid accumulation and plays a role in controlling both the quantitative and qualitative flux of fatty acids into storage TAGs. There are two distinct types of non-homologous DGAT gene families designated as DGAT1 and DGAT2, encoding proteins with DGAT activity in plants and animals. Furthermore, in certain species, such as soybean, *Vernonia galamensis*, and *Euphorbia* species, DGAT1 genes can further be divided into two distinct subclasses, designated DGAT1a and DGAT1b. Recently, the TAG biosynthetic activity of DGAT1s from a number of plant species, including soybean, *Arabidopsis*, and *Euphorbia* have been analyzed for their ability to increase the production of TAG in plants. However, for the commercial production of renewable oil in plants, the use of DGAT1 enzymes from those species have only proven to be modestly effective in increasing renewable oil production.

Disclosed herein are novel data demonstrating that certain DGAT1s have higher activity in TAG biosynthesis than other DGATs. As disclosed herein, DGAT1 proteins from *Vernonia galamensis* (Vg) were expressed in a number of cells and tissues, including, but not limited to, yeast cells, *petunia* leaves, soybean somatic embryos, and mature soybean seeds, and it was ascertained that the expression of VgDGAT1 enzymes greatly increased renewable oil production and, in particular, TAG biosynthesis and accumulation in the cells and tissues. To that end, the presently-disclosed subject matter includes methods of increasing renewable oil production in a plant, where the expression of a *Vernonia galamensis* diacylglycerol acyltransferase (VgDGAT) polypeptide increases an amount of renewable oil in the plant.

In some embodiments of the presently-disclosed subject matter, a method of increasing renewable oil production in a plant is provided that comprises transforming a plant cell with an isolated nucleic acid encoding a *Vernonia galamensis* diacylglycerol acyltransferase 1 (VgDGAT1) polypeptide, where the expression of the VgDGAT1 polypeptide increases an amount of renewable oil in the plant.

*Vernonia galamensis* is a plant in the sunflower family of significant industrial value due to high levels of oil found within the seeds of the plant. In this regard, *Vernonia galamensis* is commonly grown as a source of oil that is used in a variety of industrial applications, such as the manufacture of plastics or paints. However, the large-scale farming of *Vernonia galamensis* is typically not economically feasible, particularly outside of equatorial regions, due to poor seed yield and poor seed retention, which thus makes the plants agronomically unsuited for the industrial scale growth and processing that would be required to make use of *Vernonia galamensis* plants as a viable source of renewable seed oil. Disclosed herein, however, are data indicating that the DGAT1 genes from *Vernonia galamensis*, including *Vernonia galamensis* DGAT1a and DGAT1b genes, can be inserted into a vector and then efficiently and economically used to produce VgDGAT1 polypeptides that are capable of significantly increasing the production of renewable oils in plants that can be grown on a commercial scale.

The term "renewable oil" as used herein in relation to plants refers to oils that include or are derived from TAG and are produced by or are derived from plants or portions thereof (e.g., the organs, tissues, cells, or propagation materials of a plant) such that the oils can be replaced or replenished by the growth of a new plant or by the initial plant that produced the oil. A number of plant oils are known to those of ordinary skill in the art and include, but are not limited to, oils derived from oil seeds (e.g., canola, peanut, corn, soybean, sunflower, cottonseed, and safflower) and fixed oils such as almond oil and castor oil. Regardless of the specific type of oil, however, and as noted above, most plant oils are predominantly composed of TAGs, the synthesis of which is catalyzed, at least in part, by the activity of DGATs. As such, in some embodiments of the presently-disclosed subject matter, a method of producing a TAG is further provided that includes transforming a cell with an isolated nucleic acid that encodes a VgDGAT1 polypeptide, where the expression of the VgDGAT1 polypeptide in the cell increases an amount of TAG in the cell. In some embodiments, the cell is an animal cell, a plant cell, an algal cell, a fungal cell, or a yeast cell. In some embodiments, the cell is an algal cell selected from *C. reinherdtii*, *Chlorella*, *Scenedesmus*, *Ankistrodesmus*, *Chlorococcum*, *Boekelovia Oscillatoria*, *Amphora*, *Euglena*, and *Synechococcus* species.

The "amount" of a renewable oil, or TAG, in a cell can be determined by methods known to those of ordinary skill in the art. For example, gas chromatography-mass spectrometry, thin layer chromatography-gas chromatography, gas chromatography, near infrared (NIR) or nuclear magnetic resonance spectrophotometry, or gravimetric methods, such as Soxhlet, can be utilized to determine a total amount of renewable oil or a total amount of TAG in a sample obtained from a cell transformed with a nucleic acid encoding a VgDGAT1 polypeptide. An increase in the amount of renewable oil, or TAG, can then be measured relative to a control level of the oil, or TAG, such as an amount or range of amounts of the oil, or TAG, found in comparable samples in cells that have not been transformed with a nucleic acid encoding a VgDGAT polypeptide. In some embodiments, the increase in the amounts of renewable oils, or TAG, can be about 1%, about 2%, about 3%, about 4%, about 5%, about 6%, about 7%, about 8%, about 9%, or about 10% relative to the amounts in a control sample. In some embodiments, expression of the VgDGAT1 polypeptide increases the amount of renewable oil in the plant by at least about 2 or about 3 percent as compared to an amount of renewable oil in a control plant. In other embodiments, expression of the VgDGAT1 polypeptide increases the amount of renewable oil in the plant by at least about 5 percent as compared to an amount of renewable oil in a control plant.

In some embodiments, even though the amount of renewable oil found in the plant is increased, the protein levels in the plant are substantially unchanged as compared to a control plant. In attempts to increase amounts of oil biosynthesis in plants, any increases in amounts of renewable oils are frequently accompanied by a concomitant decrease in the levels of proteins in the plants themselves, which, in turn, decreases the value of the plant as a source of protein, such as for animal feed, for human consumption, and for many industrial applications. It has been ascertained, however, that by transforming a plant cell with a nucleic acid molecule encoding a VgDGAT1 polypeptide, plants can be produced that have increased seed oil content and little to no decrease in amount of proteins in the seeds of the plants. In some embodiments, plants are produced that have both increased seed oil content and increased amounts of proteins in the seeds of the plants, relative to control plants. In some embodiments, such an increase in the oil and protein levels in the seeds of the plants allows plant meal to be produced that is considerably higher in protein, which then allows for an increase in both the quality and value of the plant meal. Of course, any methods for measuring the protein content in a sample known to those of ordinary skill in the art, including, but not limited to, methods such as mass spectrometry, can be used to measure an amount of protein in accordance with the presently-disclosed subject matter.

In some embodiments of the presently-disclosed subject matter, the VgDGAT1 polypeptide expressed in the plant is a VgDGAT1a polypeptide (see, e.g., GENBANK® Accession No. EF653276.1, which is incorporated herein by this reference). In some embodiments, the VgDGAT1a polypeptide is encoded by a nucleic acid molecule having the sequence of SEQ ID NO: 1. In some embodiments, the VgDGAT1a polypeptide comprises the amino acid sequence of SEQ ID NO: 2.

In other embodiments of the methods described herein, the VgDGAT1 polypeptide that is expressed in the plant is a VgDGAT1b polypeptide (see, e.g., GENBANK® Accession No. EF653277, which is incorporated herein by this reference). In some of these embodiments, the VgDGAT1b polypeptide is encoded by a nucleic acid molecule having the sequence of SEQ ID NO: 3. In some embodiments, the VgDGAT1b polypeptide comprises the amino acid sequence of SEQ ID NO: 4.

In some embodiments of the presently-disclosed methods for increasing renewable oil production, the methods include the further step of transforming a plant cell with an isolated nucleic acid encoding a *Vernonia galamensis* diacylglycerol acyltransferase 2 (VgDGAT2) polypeptide (see, e.g., GENBANK® Accession No. FJ652577, which is incorporated herein by this reference; see also U.S. patent application Publication Ser. No. 12/622,045, which is also incorporated herein by reference in its entirety), where the expression of the VgDGAT1 polypeptide and the VgDGAT2 polypeptide increases an amount of renewable oil in the plant. Without wishing to be bound by any particular theory, it is believed that, in some embodiments, the co-expression of the VgDGAT1 polypeptide and the VgDGAT2 polypeptide increases the amount of renewable oil in the plant in a synergistic manner. In some embodiments, the VgDGAT2 polypeptide in encoded by a nucleic acid molecule having the sequence of SEQ ID NO: 5. In some embodiments, the VgDGAT2 polypeptide comprises the amino acid sequence of SEQ ID NO: 6.

In yet further embodiments of the presently-disclosed methods for increasing renewable oil production in a plant, a method is provided that includes transforming a plant cell with nucleic acid encoding a VgDGAT polypeptide and with a nucleic acid encoding an epoxygenase polypeptide as it has also been surprisingly discovered that such a co-expression results in an increase in renewable oil content in a plant. It is appreciated that certain VgDGAT polypeptides are capable of increasing the amount of epoxy fatty acids such as vernolic acid; however, it was previously thought that the observed increase in vernolic acid came at the expense of linoleic acid, which then resulted in no increase in the amount of oil in a plant. It has been now been determined though that certain DGAT polypeptides, including VgDGAT1 and VgDGAT2 polypeptides are able to effectively incorporates epoxy fatty acids into TAG, making a method of co-expressing a VgDGAT1 or VgDGAT2 polypeptide with an epoxygenase polypeptide a useful means to increase an amount of renewable oil in a plant.

In some embodiments of the presently-disclosed subject matter, a method of increasing an amount of renewable oil in a plant is provided that includes transforming a plant cell with a first isolated nucleic acid encoding a *Vernonia galamensis* diacylglycerol acyltransferase (VgDGAT) polypeptide and a second isolated nucleic acid encoding an epoxygenase polypeptide, where the expression of the VgDGAT polypeptide and the epoxygenase polypeptide increases an amount of renewable oil in the plant as compared to the amounts of renewable oil found in a control plant. In some embodiments, the co-expression of a VgDGAT polypeptide and an epoxygenase polypeptide allows for the production of a plant where the amount of renewable oil in the plant is increased, but where the amount of protein in the plant is substantially unchanged as compared to a control plant. In some embodiments, the amount of protein in the plant co-expressing the VgDGAT polypeptide and the epoxygenase polypeptide is increased as compared to a control plant.

In some embodiments of the presently-disclosed methods that include co-expressing a VgDGAT polypeptide and an epoxygenase polypeptide, the VgDGAT polypeptide can be a VgDGAT1a polypeptide, a VgDGAT1b polypeptide, or a VgDGAT2 polypeptide, such as those polypeptides described herein above. In some embodiments, the epoxygenase polypeptide is encoded by a nucleic acid sequence of SEQ ID NO: 19. In some embodiments, the epoxygenase polypeptide is a *Stokesia laevis* polypeptide, such as the epoxygenase described in U.S. Pat. No. 7,364,901, which is incorporated herein by this reference (see also GENBANK® Accession No. EA619792.1, which is further incorporated herein).

In some embodiments of the methods for increasing renewable oil production, transforming the plant cell with a first isolated nucleic acid and a second isolated nucleic acid comprises transforming the cell with a vector that includes the first isolated nucleic acid and a vector that includes the second isolated nucleic acid. For example, in some embodiments, a nucleic acid encoding a DGAT polypeptide can be inserted into an appropriate vector as described herein and a nucleic acid encoding an epoxygenase polypeptide can be inserted into another vector. In some embodiments, each of the vectors can then be electroporated into *Agrobacterium tumefacians* cells, which can then be used to transform cells with the vectors according to agro-infiltration methods known to those of ordinary skill in the art.

The term "isolated," when used in the context of an isolated nucleic acid or an isolated polypeptide, is a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer, et al. 1991; Ohtsuka, et al. 1985; Rossolini, et al. 1994).

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homo logs, orthologs, paralogs, fragments and other equivalents, variants, and analogs of the foregoing.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can also be a "functional fragment," in which case the fragment retains some or all of the activity of the reference polypeptide as described herein. For example, in some embodiments, a functional fragment of a VgDGAT1 polypeptide can retain some or all of the ability of the reference polypeptide to catalyze the final acylation step during TAG synthesis, such as what had been described for other DGAT1 polypeptides (see, e.g., Siloto, et al., 2009; Siloto, et al., 2009; and Xu, et al. 2008).

The terms "modified amino acid," "modified polypeptide," and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, a functional variant of a DGAT1 polypeptide retains some or all of the ability of the reference polypeptide to catalyze the final acylation step during TAG synthesis.

The term functional variant also includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitutions, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically-derivatized residue, provided that the resulting peptide maintains some or all of the activity of the reference peptide as described herein.

In some embodiments of the presently-disclosed subject matter, vectors that include one or more of the isolated nucleic acid sequences described herein are provided. In some embodiments, a vector is provided that includes an isolated nucleic acid encoding a VgDGAT1a polypeptide, a VgDGAT1b polypeptide, a VgDGAT2 polypeptide, an epoxygenase polypeptide, or combinations thereof. The term "vector" is used herein to refer to any vehicle that is capable of transferring a nucleic acid sequence into another cell. For example, vectors which may be used in accordance with the presently-disclosed subject matter include, but are not limited to, plasmids, cosmids, bacteriophages, or viruses, which can be transformed by the introduction of a nucleic acid sequence encoding a VgDGAT polypeptide described herein. Such vectors are well known to those of ordinary skill in the art. In some embodiments, the vectors of the presently-disclosed subject matter are plasmids, such as the plasmid pBI121 or the pCAMBIA1301 plasmid.

In some embodiments, the isolated nucleic acid included in the vector is operably linked to an expression control sequence. The terms "associated with," "operably linked," and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression control sequence" is used interchangeably herein with the term "expression cassette" and is used to refer to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression control sequence comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

In some embodiments, an expression control sequence is provided that comprises a "constitutive promoter," such as a 35S promoter, a figwort mosaic promoter, or the constitutive plant promoter of ubiquitin, that continually expresses a nucleic acid sequence of the presently-disclosed subject matter in all types of cells where it is inserted. For some applications, it is useful to direct the expression of a nucleic acid sequence of the presently-disclosed subject matter to different tissues of a plant. As such, in some embodiments, an expression control sequence is provided that comprises a "seed-specific promoter," such as a phaseolin, glycinin, conglycinin, seed lectin, napin, cruferin, or other seed-specific promoter that expresses a nucleic acid sequence of the presently-disclosed subject matter only in seeds of a desired plant.

The presently-disclosed subject matter also provides transgenic plant cells or plants that have been transformed with one or more of the vectors disclosed herein. As used herein, the term "plant cell" is understood to mean any cell derived from a monocotyledonous or a dicotyledonous plant and capable of constituting undifferentiated tissues such as calli, differentiated tissues such as embryos, portions of monocotyledonous or dicotyledonous plants, monocotyledonous or dicotyledonous plants or seed. The term "plant" is understood to mean any differentiated multi-cellular organism capable of photosynthesis, including monocotyledons and dicotyledons. In some embodiments of the methods for increasing renewable oil production in a plant, the plant is selected from: *Arachis hypogaea, Borago officinalis, Brassica campestris, Brassica napus, Brassica rapa, Camelina sativa, Cannabis sativa, Carthamus tinctorius, Cocos nucifera, Crambe abyssinica, Cuphea* species, *Glycine max, Gossypium hirsutum, Gossypium barbadense, Gossypium herbaceum, Helianthus annuus, Linum usitatissimum, Oenothera biennis, Olea europaea, Oryza sativa, Perilla frutescens, Ricinus communis, Salvia hispanica, Sesamum indicum, Sinapis alba, Theo-*

*broma cacao, Triticum* species, *Zea mays, Juglans* species, or *Prunis dulcis*, or a cell from such plants.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then injected into a plant by placing the tip of a syringe against the underside of a leaf while gentle counter-pressure is applied to the other side of the leaf. The *Agrobacterium* solution is then injected into the airspaces inside the leaf through stomata. Once inside the leaf, the *Agrobacterium* transforms the gene of interest to a portion of the plant cells where the gene is then transiently expressed.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold or tungsten particles, wherein the particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-2 cDNA Cloning.

Partial *Vernonia galamensis* and *Euphorbia lagascae* diacylglycerol acyltransferase (DGAT) cDNA fragments wee obtained from RNA of developing embryos using an Access RT-PCR System (Promega Co., Madison Wis.). The PCR mixtures contained 1 µg of total RNA template, 0.2 mM dNTPs, 2.5 U of AMV reverse transcriptase, 2.5 U of Tfl polymerase and 1 µM each of two degenerate primers described below. Reaction mixtures were incubated in a thermocycler (Perkin Elmer, Waltham Mass., Model 2400) for 45 minutes at 48° C., followed by 2 minutes at 94° C. and 40 cycles of 30 s at 94° C., 30 s at 50° C. and 1 minute at 72° C. The PCR primers used (DGATF, 5'-GCTCCYACWTTGT-GTTATSARC-3'; SEQ ID NO: 7, and DGATR, 5'-CCAYT-TRTGRACRGGSATATTCCA-3'; SEQ ID NO: 8) represent two peptide sequences, [APTLCYE/Q] (SEQ ID NO: 9) and [WNI/MPVHKW] (SEQ ID NO: 10), which are the conserved regions in amino acid sequences of DGATs of *Arabidopsis thaliana* and *Mus musculus*. The amplified products of approximately 380 bp were fractionated on a 1% agarose gel, extracted from the gel using Quiaquick Gel Extraction Kit (Qiagen Inc., Valencia, Calif.) and subcloned into the pGEM-T Easy vector (Promega Co., Madison, Wis.) according to the manufacturer's instructions. The DNA inserted was sequenced in both directions.

For determination of the full-length cDNA sequence, a RACE (Rapid Amplification of cDNA Ends) strategy was applied. A cDNA was synthesized from poly(A)+RNA of developing seeds of *S. laevis* using a Smart RACE cDNA Amplification Kit (BD Biosciences Clontech, San Jose, Calif.). The following two primers were then designed from the sequence information of the partial cDNA fragment of *Vernonia galamensis* DGAT; VerDaF: 5'-TCGAAAGGGT-TGGGTGTTACGGCAACTG-3' (SEQ ID NO: 11), and VerDaR: 5'-CAGTTGCCGTAACACCCAACCCTTTCGA-3' (SEQ ID NO: 12), and *Euphorbia lagascae* DGAT; Euph5: 5'-CAACTTGACAAACTGACGGAACACCC-3' (SEQ ID NO: 13), and Euph3: 5'-GGGTGTTCCGTCAGTTTGT-CAAGTTG-3' (SEQ ID NO: 14). The 5'-half and 3'-half of the cDNAs were amplified using the PCR conditions described in the user manual of the kit. Fractionation of the amplified fragments, cloning and sequencing were carried out as described above.

For soybean DGAT cloning, a BLAST search of the sequence database using the *Arabidopsis* protein sequence identified soybean EST (Gm-c 1036-7949). The EST was fully sequenced in both directions. Since the EST lacked the 5' end of the cDNA, it was obtained by 5' RACE with appropriate nested primers using a Smart RACE cDNA Amplification kit (BD Biosciences Clontech, San Jose, Calif.). A cDNA was synthesized from poly(A)+RNA of developing seeds of the soybean cultivar, Jack. The following two primers were then designed from the sequence information of the cDNA of the EST; SoyD5-1: 5'-GCGTAAAGAAGGTTTCCCT-TGAGAGGATGC-3' (SEQ ID NO: 15), and SoyD3-1: 5'-GTTGCCCCTACATTATGTTACCAGCCAAGC-3' (SEQ ID NO: 16). The 5'-half and 3'-half of the cDNAs were amplified using the PCR conditions described in the user manual of the kit. In order to obtain the second possible DGAT sequence, another set of primers were designed that were; SoyD5-2: 5'-GAAAACACGCTCGGTCTTCTTC-3' (SEQ ID NO: 17), and SoyD3-2: 5'-TACAATTGCCAGAG-GAGAGTTG-3' (SEQ ID NO: 18). Fractionation of the amplified fragments (1.5 kb), cloning and sequencing were carried out as described above.

Expression in Insect Cells.

The expression in Sf9 cells was tested with the Bac-to-Bac expression system (Gibco BRL, Carlsbad, Calif.), and the recombinant baculovirus was prepared following their instruction manual. Sf9 cells were then infected by the baculovirus possessing *Vernonia* or *Euphorbia* DGAT and cultured for 4 days and the cells were collected. Another set of cultured cells was infected by the baculovirus without cloned genes as a control. Their lipids were extracted with chloroform:methanol (2:1), lipid fractions were separated with thin layer chromatography (TLC) using hexane: ethyl ether: acetic acid, 90:10:1, followed by visualization with primulin and the fatty acids were methylated and analyzed with capillary gas chromatography (GC).

Yeast Microsome Assays.

*Vernonia, Arabidopsis, Glycine*, and *Euphorbia* DGATs were cloned into yeast vector pYES2 (Invitrogen, Carlsbad, Calif.). The constructs along with the void vector were used to transform yeast (*Saccharomyces cerevisiae*) strain INVSc1 (Invitrogen, Carlsbad, Calif.). Transformed yeasts were cultured and the microsome fractions were prepared according to standard protocols (Dahlqvist et al., 2000). The reaction mixture (100 μL) contained 20 mM radiolabeled linoleic acid CoA, 300 mM dioleyl diacylglycerol, 0.02% Tween 20, 100 mM Tris-HCl (pH 7.1), 1 mM $MgCl_2$, 0.5 mM CoASH, 0.5 mM ATP and microsomes (corresponding to 50 μg protein). The suspension was incubated at 30° C. with shaking (100 rpm) for 1 hour. The reaction was stopped by first placing the test tubes with the reaction mixture in ice and followed by adding 100 μg of soybean triacylglycerol as carrier. The lipid was then extracted with chloroform:methanol (2:1, v/v). Samples were subsequently loaded on TLC plates and the radioactive bands were detected by phosphorimaging and scintillated. For identification of radioactive products, methylated fractions were analyzed by TLC with a hexane:MTBE (methyl tert-butyl ether):acetic acid (85:15:1, v/v/v) solvent system.

Lipid Analysis.

Samples prepared as described above were frozen in liquid $N_2$, stored at −80° C. and then lyophilized. Weighed samples were transferred to glass test tubes and tri-heptadecanoin (tri-17:0) was added at 10 μg/mg tissue as a standard. The samples were finely ground, and 1-2 mL of chloroform and methanol (2:1) containing 0.001% butylated hydroxytoluene (BHT) was added and the samples were ground further. After a brief spin, the lower layer ($CHCl_3$ phase) was then transferred into a new glass tube, and the samples were divided into two aliquots. One was used for TLC and the other directly for GC analysis.

For GC analysis, samples were dried with $N_2$, 0.5 mL of 0.5 M sodium methoxide ($NaOCH_3$) in methanol was added and incubated for at least 15 minutes with shaking at 22° C. 0.5 mL of isooctane containing 0.001% BHT was added to each tube and mixed well. Phase separation was obtained with centrifugation or adding aqueous 0.9% KCl if needed. The top layer was extracted and transferred into GC auto-sampler vials. The fatty acid methyl esters (FAMEs) were analyzed with gas chromatography on a Varian CP-3800 GC with a 24 m×0.25 mm ID CP-Select CB for FAME analysis using a fused silica column with a 0.25 μm film thickness. The temperature program was 90° C. for 1 min., then to 155° C. at 20° C./min. with no hold, then to 175° C. at 3.6° C./min. with no hold and finally to 250° C. at 12° C./min. holding for one min.

For separation of individual lipid classes by TLC, the samples ($CHCl_3$ lipid extracts) were concentrated to about 50-100 μL. Ten μL of the sample was loaded in a narrow band in lanes of silica gel 60 (Whatman LK6D Silica gel 60A) TLC plates 1 cm from the bottom of the plates. The plates were put in a chamber with chloroform:methanol:water (65:25:4, v/v)+0.0001% BHT for running until the first solvent reached ½ up the plate (~10 cm). Then, the plate was moved into the second solvent, hexane:diethyl ether:acetic acid (100:100:2, v/v)+0.0001% BHT and developed until solvent was approximately 1 cm from the top. After development, the plate was dried, and subsequently sprayed with 0.005% primulin in 80% acetone, followed by visualizing under UV light and marking the bands of interest. The bands were scraped and transferred to a Pasteur pipette with a glass wool plug washed with $CHCl_3$:$CH_3OH$. The lipid samples were eluted with 0.5 mL of $CHCl_3$:$CH_3OH$+0.001% BHT twice. Finally, eluted lipid samples were analyzed by GC as described above.

Seed-Specific Expression Vector Construction and Soybean Somatic Embryo Transformation.

An expression vector for soybean transformation was constructed using the plant expression vector pCAMBIA1301 containing the hygromycin resistance gene as a selector and the GUS gene as a reporter (Cambia, ACT, Australia; GENBANK® No. AF234297). The coding sequences for VgDGAT1 and VgDGAT2 were amplified by a high fidelity polymerase (Invitrogen, Carlsbad, Calif.) using end-specific primers containing restriction sites. The amplification product was then subcloned into the respective sites of pPHI4752 vector containing a phaseolin promoter, which confers strong seed-specific expression of transgenes (Slightom et al., 1983). The phaseolin promoter cassette containing the coding region of each target gene was transferred into the corresponding sites of the binary pCAMBIA1301, T-DNA vector. These recombinant expression vectors were subsequently introduced into somatic embryos of soybean (cv. 'Jack') using the particle bombardment method of transformation.

Soybean somatic embryo induction and culture was carried out using a protocol modified from prior procedures (Collins et al., 1991; Finer and Nagasawa, 1988a; Finer and Nagasawa, 1988b; Samoylov et al., 1998; Trick et al., 1997). Briefly, immature soybean seeds at 3-5 mm length were dissected, and cotyledons were placed on D40 (40 mg/L 2,4-D in MS media) solid medium for one-month induction of somatic embryo induction. The induced embryos were transferred to D20 plates for proliferation. The globular embryogenic cultures from D20 (20 mg/L 2,4-D in MS media) plates were then moved into FN (Finer and Nagasawa, 1988a) liquid medium for one-month suspension culture. Small embryo clumps were selected for particle bombardment gene delivery.

Plasmid DNA/gold preparation for the particle bombardment was conducted according to standard protocols (Trick et al., 1997). A DuPont Biolistic PDS 1000/HE instrument (helium retrofit) was used for all transformations. After bombardment the embryo clumps were transferred into FN liquid medium containing 30 mg/L hygromycin for selective culture for four to five weeks. The positive transformed embryos obtained by hygromycin selection were then moved into fresh FN liquid medium for culture and simultaneously for GUS test and identification of the transgene presence by PCR. The PCR-positive transgenic embryo lines were transferred into maturation medium (SHaM) (Schmidt et al., 2005) for three to five weeks. Matured individual embryos were desiccated for 4-7 days, and then were placed on ½ strength MS solid medium for germination. Germinated plantlets were transferred to closed sterile soil cups for growth in a culture room under 23:1 (light:dark) photoperiod cycle and 25° C. Once seedlings reached a proper height (approximately 13 cm), the seedlings were transferred to a greenhouse for flowering and seed set under a 16:8 (light:dark) cycle, 25/21° C.

For the transgenic lines, one set of matured somatic embryos were sampled for lipid extraction and subsequent GC analysis. The rest of the matured somatic embryos were desiccated, germinated and grown to maturity in a greenhouse. Mature seeds were harvested from each regenerated soybean plant separately. Seed were chipped for genotyping by PCR and fatty acid analysis by GC. TAG levels of the somatic embryos and the $1^{st}$ generation zygotic seeds were assessed by addition of tri-heptadecanoin to seed/embryo chips of known dry weight after lyophilization and GC analysis. Lines showing higher levels by this assessment and the presence of the introduced genes by PCR were selected for further analysis.

Determination of Protein and Oil Levels.

The protein and oil levels of subsequent generations of progeny of lines selected for higher oil contents were determined in bulk by near infrared (NIR) spectroscopy using a Perten (Springfield, Ill.) DA7200. This NIR seed analyzer was calibrated with greater than one hundred soybean samples varying in protein and oil levels with the protein and oil levels of the calibration samples determined by combustion for protein and Soxhlet for oil (AOAC, 1995; de Castro and Priego-Capote, 2010; Rotundo et al., 2011; Soxhlet, 1879). Protein levels were calculated as total nitrogen×6.25. Every set of NIR determinations was validated by running 13-20 calibration standards of known values and adjusting the bias settings if needed such that the protein and oil readings are in ±1% of the wet chemistry values. These core set of standards were also analyzed for protein and oil by Kjeldahl, acid hydrolysis (Mojonnier flask method) and NMR (Ashraf-Khorassani et al., 2002; Hakoda et al., 2011; Ullah et al., 2011). Gravimetric determination of moisture levels of seed samples involved drying samples in a convection oven at 103° C. for 36-72 h or until the weights stopped changing.

Example 1

Expression of Diacylglycerol Acyltransferase in Cells

To examine the oil synthesis activity of TAG biosynthetic enzymes, five cDNA clones were isolated, namely: Soybean DGAT1a and 1b, *Euphorbia* DGAT1a, and *Vernonia* DGAT1a and 1b, and it was found that *Glycine max, E. lagascae* and *V. galamensis* have at least two DGAT1s. Full-length DGAT1 cDNAs were then produced from all three species, including GmDGAT1a, GmDGAT1b, ElDGAT1a, VgDGAT1a and VgDGAT1b cDNAs.

Figure 2:
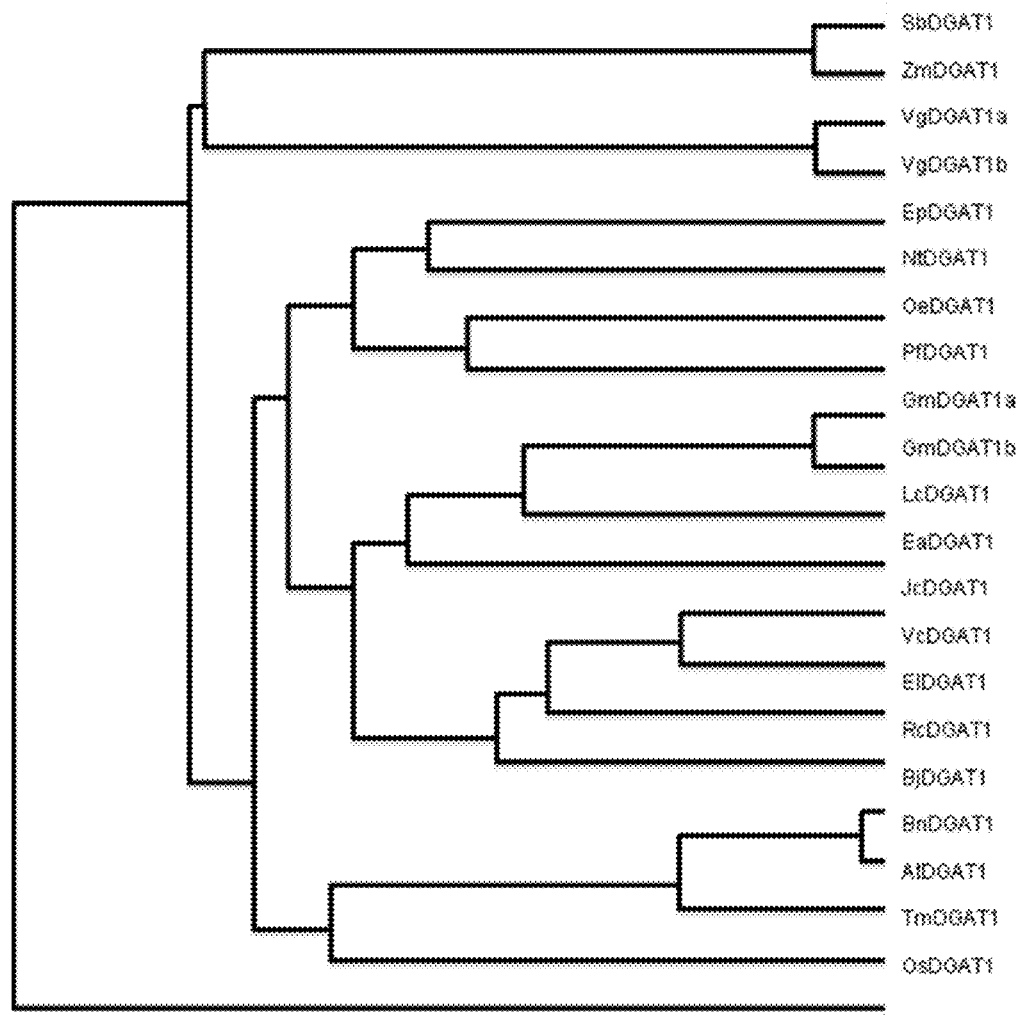
FIG. 2 is a schematic diagram showing the phylogenetic relationships between soybean (Gm), *Vernonia* (Vg), *Euphorbia* (El) and *Arabidopsis* (At) DGAT1s and also showing the association of those DGAT1s with other related DGAT1s.

In previous studies of DGAT1s of plants accumulating high levels of industrially valuable epoxy fatty acids, it was found that two DGAT1s have much more activity than other known plant DGAT1s. In particular, it was found that both *Vernonia galamensis* and *Euphorbia lagascae* accumulate 60% or more of an epoxy fatty acid in their seed oil. Furthermore, in experiments relating to the expression of DGAT1 from *Vernonia* and *Euphorbia* in insect cells, a much higher accumulation of TAG was found in the *Vernonia* DGAT1 expressing cells than in the *Euphorbia* DGAT1 expressing cells (Hatanaka et al., 2003); however, that information and data was not sufficient to conclude that *Vernonia* DGAT1 had any unique capacity for TAG synthesis in plants as the *Vernonia* DGAT1 was only compared to one other DGAT and it was thought that the transcripts for the *Vernonia* DGAT1s were accumulating in insect cells at levels higher that the *Euphorbia* DGAT1 transcript levels. As such, to further examine the TAG biosynthetic activity of these DGATs, the TAG biosynthetic activity of a number of DGAT1s were analyzed in yeast using the above-described system for microsomal analysis, which utilizes 300-fold lower concentrations of microsomes compared to most studies, and results in lower background and more accurate activity determinations than previous methods. In the yeast system, six DGATs were studied: the five DGATs mentioned above and *Arabidopsis* DGAT1. Upon analysis of the results from these experiments, it was observed that the *Arabidopsis* DGAT1 showed only slightly higher activity than the vector control (FIG. 1) as did the *Euphorbia* DGAT1 (data not shown). The soybean DGAT1s showed moderately higher activity, while both the VgDGAT1a and VgDGAT1b appeared to have unusually high activity in synthesis of oil or TAG, and were therefore thought to be useful for increasing renewable oil production in a number of species, including plant species. This finding was believed to be consistent with a unique grouping of VgDGAT1a and VgDGAT1b sequences compared to other DGATs (see, e.g., Yu et al., 2008; FIG. 2).

Example 2

Figure 3:
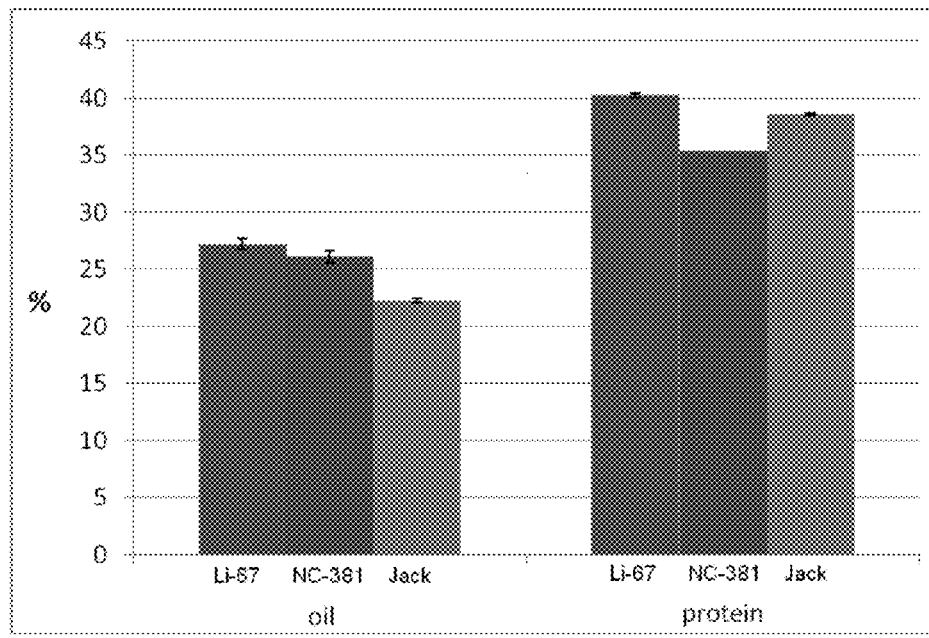
FIG. 3 is a graph showing oil and protein levels of mature soybean seeds that were produced on a research farm from a line expressing a *Vernonia galamensis* DGAT1a (Li-67), a high-oil content line of soybeans from breeding (NC-381), and a control line (Jack)

Expression of *Vernonia galamensis* Diacylglycerol Acyltransferase 1a (VgDGAT1a) in *Petunia* Leaves and in Soybean Somatic Embryos To further examine the ability of VgDGAT1s to increase renewable oil production, particularly in plants, VgDGAT1a was further expressed in *petunia* leaves and in soybean somatic embryos. Briefly, soybean somatic embryos expressing VgDGAT1a were regenerated, grown out in a greenhouse and mature T2 seeds were collected. The protein and oil content of the mature seeds was then measured and many of the VgDGAT1a transformed soybean seeds showed 3-5% increases in oil content per seed dry weight, most without any decrease in protein levels. Seeds of these higher oil soybean lines were grown out in both greenhouse and field environments and progeny were again analyzed for protein and oil contents. Again 3-5% increases in oil content per seed dry weight were observed and little or no decrease in protein levels was seen (FIG. 3; Table 1).

TABLE 1

Soybean oil and protein levels of mature seeds produced on a research farm in a line expressing a *Vernonia galamensis* VgDGAT1a, Li-67, versus a high oil line from breeding, NC-381 and control line, 'Jack'. SE = standard errors.

| Line | Protein | SE | Oil | SE |
|---|---|---|---|---|
| Li-67 | 40.2 | 0.5 | 27.2 | 0.5 |
| NC-381 | 35.4 | 0.03 | 26.1 | 0.2 |
| Jack | 38.6 | 0.13 | 22.3 | 0.2 |

Figure 4:
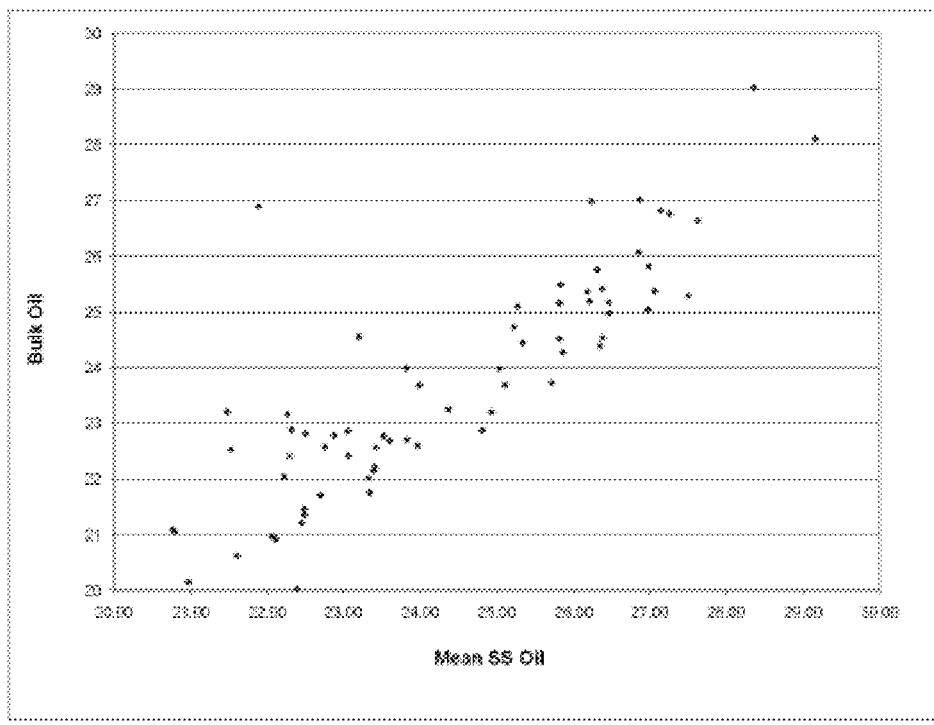
FIG. 4 is a graph showing soybean oil levels of mature seeds expressing a *Vernonia galamensis* DGAT1a versus high oil lines from breeding and regular soybeans determined by single seed (SS) and bulk seed analyses.
Figure 5:
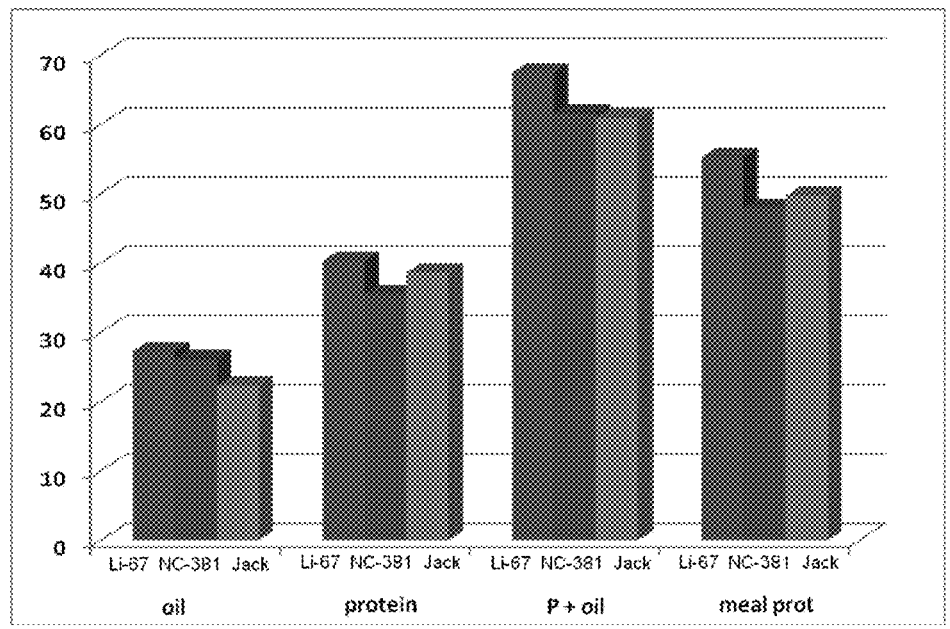
FIG. 5 is a graph showing soybean oil and protein levels and calculated meal protein levels of mature seeds produced on a research farm from a line expressing a *Vernonia galamensis* VgDGAT1a (Li-67), a high oil line from breeding (NC-381), and a control line (Jack)

These increases in oil and oil+protein were then corroborated by oil and protein analyses of individual seeds of plants from these lines by an independent set of analyses backed by standard wet chemical determination of protein and oil levels (FIG. 4). The estimated meal protein levels of such lines were also believed to be higher making meal more valuable for animal feed, food, and many industrial applications (FIG. 5).

Figure 6:
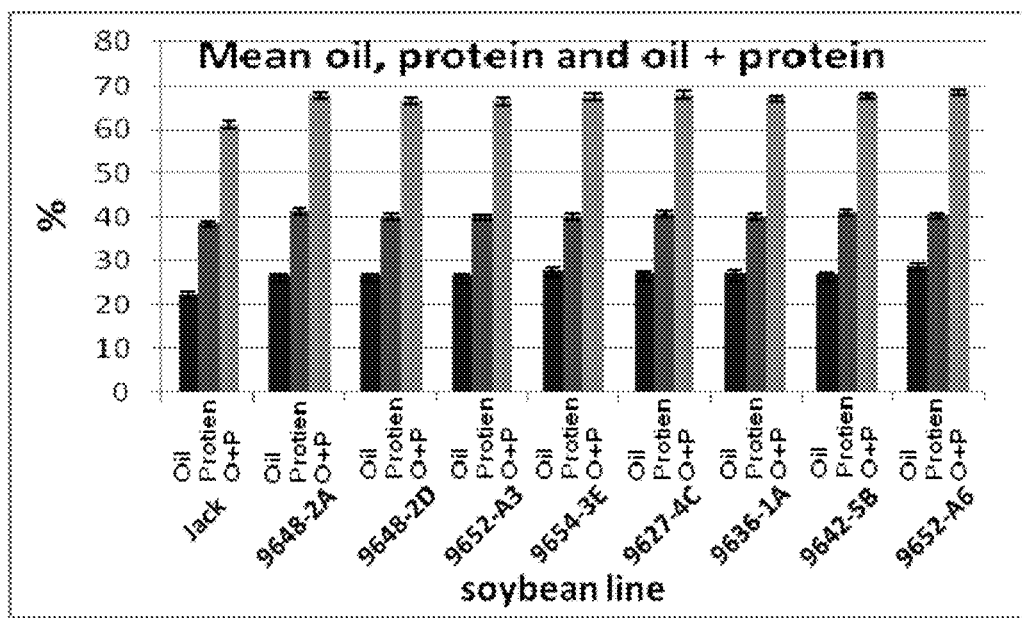
FIG. 6 is a graph showing the percentages of mean oil, protein, and oil and protein (O+P) in mature soybean seeds produced on a research farm over three years from a control line (Jack) and from various lines expressing VgDGAT1a (9648-2A; 9648-2D; 9652-A3; 9654-3E; 9627-4C; 9636-1A; 9642-5B; and 9652-A6)

To further examine the lines, and their commercial feasibility, the lines highest in oil and oil+protein were grown out in the field following standard farming conditions, and again showed stable increases in oil and oil+protein with several lines consistently about 7% higher in oil+protein than the parental line or normal high yielding soybean cultivars (FIG. 6; Table 2), indicating that expression of a VgDGAT1 polypeptide is useful for increasing an amount of renewable oil production in a plant.

TABLE 2

Soybean oil and protein levels of mature seeds produced on a research farm in various line expressing a *Vernonia galamensis* VgDGAT1a.

| Line | Protein | SE | Oil | SE |
|---|---|---|---|---|
| vector contr | 38.0 | 0.4 | 22.4 | 0.3 |
| control | 38.2 | 0.1 | 21.5 | 0.3 |
| 9648-2-A | 41.6 | 0.1 | 25.2 | 0.1 |
| 9652-3-F | 40.8 | 0.3 | 24.1 | 0.1 |
| 9652-1-D | 44.5 | 0.4 | 18.3 | 0.3 |
| 9652-A-3 | 40.0 | 0.1 | 24.3 | 0.1 |
| 9652-A-4 | 37.3 | 0.3 | 25.2 | 0.3 |
| 9652-A-6 | 36.5 | 0.3 | 26.0 | 0.2 |
| 9652-A-7 | 39.3 | 0.2 | 24.7 | 0.1 |
| 9652-2-B | 39.3 | 0.2 | 24.2 | 0.2 |
| 9652-3-B | 39.0 | 0.1 | 24.7 | 0.2 |
| 9652-3-D | 38.8 | 0.1 | 25.1 | 0.3 |
| 9654-3-B | 39.9 | 0.3 | 24.5 | 0.4 |
| 9654-3-C | 42.1 | 0.1 | 25.1 | 0.1 |
| 9654-3-E | 43.4 | 0.0 | 25.1 | 0.0 |
| 9654-3-F | 41.3 | 0.0 | 24.5 | 0.1 |

Example 3

Effect of Co-Expression of *Vernonia galamensis* Diacylglycerol Acyltransferase 1 and 2 and *Stokesia Laevis* Epoxygenase on Oil Content of Transgenic Plants To assess the effect of co-expressing *Vernonia galamensis* diacylglycerol acyltransferase 1 and 2 (VgDGAT1 & 2) and *Stokesia laevis* epoxygenase (SlEPX) polypeptide in transgenic plants, transgenic plant regeneration and identification of the transgenic expressions were first performed as described in detail previously (Li et al., 2010). Briefly, the expression vector for soybean transformation was constructed using the pCAMBIA1301 vector containing a hygromycin resistance gene and the GUS gene as a reporter (Cambia, ACT, Australia; GENBANK® No. AF234297). The ORFs of *Stokesia epoxygenase* (SlEPX) and *Vernonia* DGATs (VgDGAT1a and VgDGAT2) were each driven by a seed-specific phaseolin promoter. The construct was introduced into soybean somatic embryo cultures using a particle delivery system (Gene Gun). Positive somatic embryos after hygromycin selection culture were confirmed by PCR, and then cultured to mature soybean somatic embryos. Matured embryos were subsequently germinated in germination media, and the seedlings were transferred to soil pots for growth and production of the transgenic seeds, which were subsequently grown on a research farm for two generations. The soybean seeds were then collected for analysis from the soybean plants grown on the farm, and protein and oil levels were analyzed with a Perten DA7200 NIR seed analyzer with extensive calibrations for soybean seeds. The NIR levels were verified by Soxhlet gravimetric determination of lipid levels and Kjeldahl analysis of nitrogen. Each replicate was measured by three times. A total of 6 replicates were measured for each line.

Figure 7:
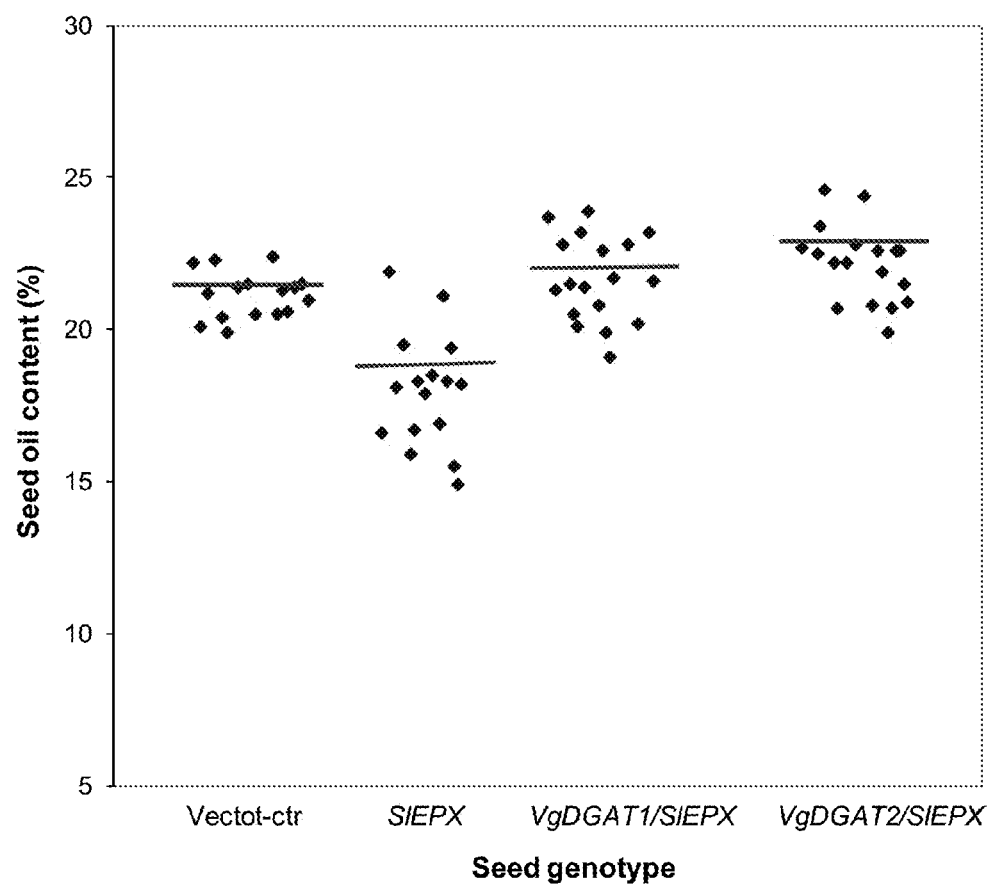
FIG. 7 is a graph showing seed oil contents from a control soybean line (Vector-ctr) and from transgenic soybean lines expressing either a *Stokesia laevis* epoxygenase transgene (SlEPX), a VgDGAT1a transgene and a SlEPX transgene, or a VgDGAT2 transgene and a SlEPX transgene, where each data point represents seed oil content in whole seed samples from individual transgenic plants that were grown, and where horizontal bars indicate the mean for each dataset.

It has previously been observed that additional seed-specific expression of either VgDGAT1a or VgDGAT2 in SlEPX-transgenic soybeans results in vernolic acid accumulation up to 17% and 27.8% in the seeds and normal fatty acid profiles, with the exception of a decreased 18:2 level (Li et al., 2010). Upon analysis of the results from the present experiments, however, it was surprisingly found that co-expression of VgDGAT1a or VgDGAT2 with SlEPX was capable of increasing total seed oil content in the transgenic plants. As shown in FIG. 7, the reduced oil content observed in seeds expressing the SlEPX gene alone changed markedly when either VgDGAT1a or VgDGAT2 was co-expressed with SlEPX. In these double-transgenic plants, seed oil contents were returned to normal levels (20-21%), similar to levels in the non-transgenic and the vector control soybeans, regardless of the level of vernolic acid accumulation. Furthermore, although statistical analysis (t-test) showed that the difference of seed oil level was not significant (P<0.05) between the control and the double transgenic lines, a significant difference (P<0.05) was found between the controls and SlEPX-expressing lines and it was also observed that a number of the double transgenic lines produced higher seed oil levels (22.4%). Moreover, the VgDGAT-mediated restoration of oil levels in SlEPX-transgenic soybean seeds showed stable inheritance in two subsequent generations examined so far under field conditions.

Figure 8:
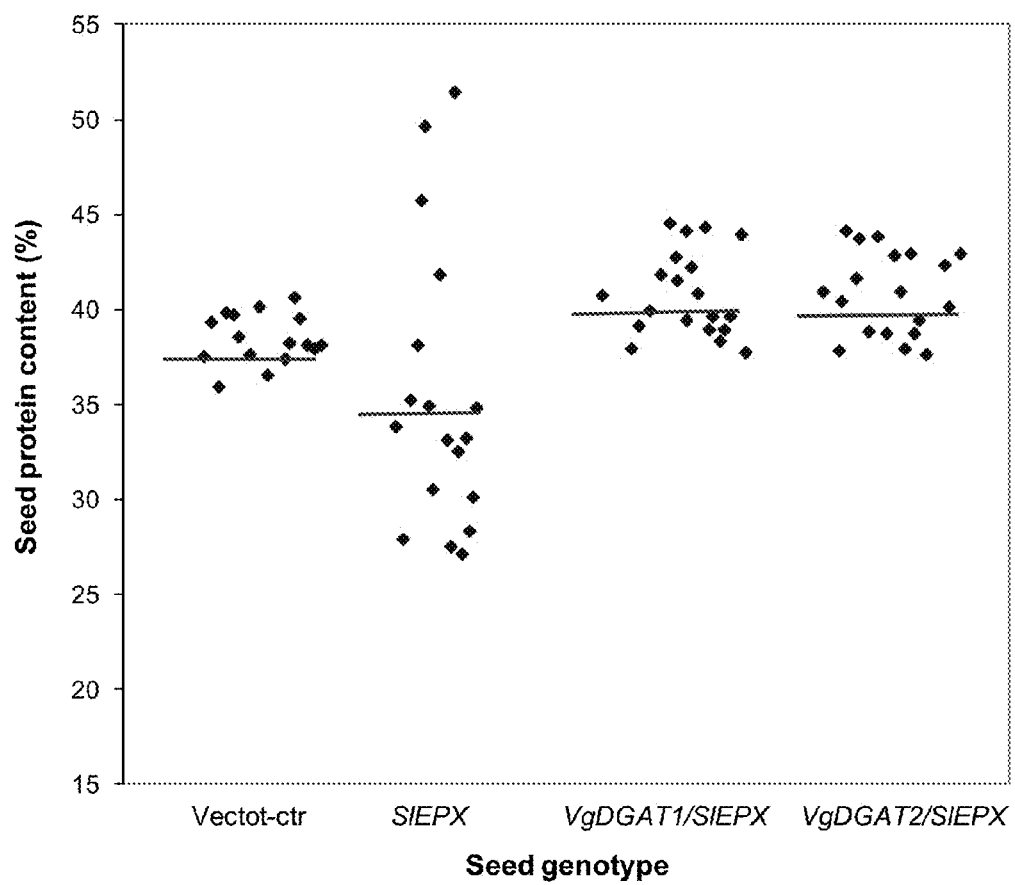
FIG. 8 is a graph showing seed protein content from a control soybean line (Vector-ctr) and from transgenic soybean lines expressing either a *Stokesia laevis* epoxygenase transgene (SlEPX), a VgDGAT1a and a SlEPX transgene, or a VgDGAT2 and a SlEPX transgene, where each data point represents seed protein content in whole seed samples from individual transgenic plants that were grown, and where horizontal bars indicate the mean for each dataset.

In soybean seeds, the oil content is usually inversely correlated with protein levels (Clemente and Cahoon, 2009). However, in conjunction with a reduction in oil content in the SlEPX-transgenic seeds, it was observed that seed protein levels showed dramatic changes, increasing in some transgenic lines and decreasing in others (FIG. 8). As in the case of total oil content, however, seed protein levels in the transgenic lines co-expressing SlEPX and either of the VgDGATs were restored to normal levels (approximately 40%) regardless of higher or lower protein level in soybean seeds only expressing SlEPX. Again, no statistical difference (P<0.05) in seed protein level was found between the control and the VgDGAT-SlEPX co-expressing lines, but significant differences (P<0.05) were detected between the control and SlEPX expressing lines and a number of the double transgenic lines showed higher seed protein levels than what was observed in the control lines. These data indicate that VgDGATs are also able to overcome the unstable seed protein accumulation caused by SlEPX and/or vernolic acid accumulation in soybean seeds, further indicating that co-expression of VgDGAT and SlEPX polypeptides are useful for increasing an amount of renewable oil in a plant.

Throughout this document, various references are mentioned. All such references are incorporated herein by reference, including the references set forth in the following list:

REFERENCES

1. Anon. 2010. Historical Oil Prices [Online].
2. Bates, P. D., T. P. Durrett, J. B. Ohlrogge, and M. Pollard. 2009. Analysis of Acyl Fluxes through Multiple Pathways of Triacylglycerol Synthesis in Developing Soybean Embryos. Plant Physiol. 150:55-72.
3. Baud, S., and L. Lepiniec. 2009. Regulation of de novo fatty acid synthesis in maturing oilseeds of *Arabidopsis*. Plant Physiology and Biochemistry 47:448-455.
4. Baud, S., S. Wuilleme, A. To, C. Rochat, and L. Lepiniec. 2009. Role of WRINKLED1 in the transcriptional regulation of glycolytic and fatty acid biosynthetic genes in *Arabidopsis*. Plant Journal 60:933-947.
5. Bewley, J., and M. Black. 1994. Seeds: Physiology of Development and Germination. 2nd ed. Plenum Press, New York.
6. Cases, S., S. J. Stone, P. Zhou, E. Yen, B. Tow, K. D. Lardizabal, T. Voelker, and R. V. Farese, Jr. 2001. Cloning of DGAT2, a second mammalian diacylglycerol acyltransferase, and related family members. J Biol Chem 276:38870-6.
7. Cases, S., S. J. Smith, Y. Zheng, H. M. Myers, S. R. Lear, E. Sande, S. Novak, C. Collins, C. B. Welch, A. J. Lusis, S. K. Erickson, and R. V. Farese, Jr. 1998. Identification of a gene encoding an acyl CoA:diacylglycerol acyltransferase, a key enzyme in triacylglycerol synthesis. Proceedings of the National Academy of Sciences of the United States of America 95:13018-13023.
8. Cernac, A., and C. Benning. 2004. WRINKLED1 encodes an AP2/EREB domain protein involved in the control of storage compound biosynthesis in *Arabidopsis*. The Plant Journal 40:575-585.
9. Clemente, T. E., Cahoon, E. B., 2009. Soybean Oil: Genetic Approaches for Modification of Functionality and Total Content. Plant Physiol. 151, 1030-1040.
10. Dahlqvist, A., U. Stahl, M. Lenman, A. Banas, M. Lee, L. Sandager, H. Ronne, and S. Stymne. 2000. Phospholipid:diacylglycerol acyltransferase: an enzyme that catalyzes the acyl-CoA-independent formation of triacylglycerol in yeast and plants. Proc Natl Acad Sci USA 97:6487-92.
11. Dahmer, M. L., G. B. Collins, and D. F. Hildebrand. 1991. Lipid concentration and composition of soybean zygotic embryos maturing in vitro and in planta. Crop Sci. 31:735-740.
12. Dewey, R. E., R. F. Wilson, W. P. Novitzky, and J. H. Goode. 1994. The AAPT1 Gene of Soybean Complements a Cholinephosphotransferase-Deficient Mutant of Yeast. Plant Cell 6:1495-1507.
13. Egli, D. B. 2008a. Comparison of corn and soybean yields in the United States: Historical trends and future prospects. Agron. J. 100:S79-S80.
14. Egli, D. B. 2008b. Soybean yield trends from 1972 to 2003 in mid-western USA. Field Crops Res. 106:53-59.
15. Focks, N., and C. Benning. 1998. wrinkled1: A Novel, Low-Seed-Oil Mutant of *Arabidopsis* with a Deficiency in the Seed-Specific Regulation of Carbohydrate Metabolism. Plant Physiol. 118:91-101.
16. Franzosi, G., E. Battistel, M. Santoro, and R. Iannacone. 1998. LPAAT and DAGAT Activity and Specificity in Rapeseed (*Brassica napus* L. var. Canola) and Sunflower (*Helianthus annuus*) Developing Seeds. J. Sanchez, et al. (ed.) Advances in Plant Lipid Research, Sevilla, Spain. Universidad De Sevilla. Secretariado de Publicaciones.
17. Gavilano, L. B., N. P. Coleman, L. E. Burnley, M. L. Bowman, N. E. Kalengamaliro, A. Hayes, L. Bush, and B. Siminszky. 2006. Genetic Engineering of *Nicotiana tabacum* for Reduced Nornicotine Content. J. Agric. Food Chem. 54:9071-9078.
18. Goldberg, R. B., S. J. Barker, and L. Perez-Grau. 1989. Regulation of gene expression during plant embryogenesis. Cell 56:149-160.
19. Harwood, J. L. 1997. Plant Lipid Metabolism, p. 237-272, In P. M. Dey and J. B. Harborne, eds. Plant Biochemistry. Academic Press, London.
20. Harwood, J. L., and R. A. Page. 1994. Biochemistry of oil synthesis., p. 165-194, In D. J. Murphy, ed. Designer Oil Crops. VCH, Weinheim.
21. Hildebrand, D. F., R. Li, and T. Hatanaka. 2008. Genomics of soybean oil traits, p. 185-210, In G. Stacey, ed. Genetics and Genomics of Soybean. Springer, N.Y.
22. Hiramine, Y., H. Emoto, S. Takasuga, and R. Hiramatsu. 2010. Novel acyl-coenzyme A:monoacylglycerol acyltransferase (MGAT) plays an important role in hepatic triacylglycerol secretion. J. Lipid Res. 51:1424-1431.
23. Hiraoka, M., A. Abe, and J. A. Shayman. 2002. Cloning and Characterization of a Lysosomal Phospholipase A2, 1-O-Acylceramide Synthase. J. Biol. Chem. 277:10090-10099.
24. Hobbs, D. H., and M. J. Hills. 2000. Expression and characterization of diacylglycerol acyltransferase from *Arabidopsis thaliana* in insect cell cultures. Biochem Soc Trans 28:687-9.
25. Hobbs, D. H., C. Lu, and M. J. Hills. 1999. Cloning of a cDNA encoding diacylglycerol acyltransferase from *Arabidopsis thaliana* and its functional expression. FEBS Lett 452:145-9.
26. Jackson, F. M., L. Michaelson, T. C. M. Fraser, A. K. Stobart, and G. Griffiths. 1998. Biosynthesis of triacylglycerol in the filamentous fungus *Mucor circinelloides*. Microbiology 144:2639-2645.
27. Kalinski, A., D. S. Loer, J. M. Weisemann, B. F. Matthews, and E. M. Herman. 1991. Isoforms of soybean seed oil body membrane protein 24 kDa oleosin are encoded by closely related cDNAs. Plant-molecular-biology 17:1095-8.
28. Kamisaka, Y., S. Mishra, and T. Nakahara. 1997. Purification and characterization of diacylglycerol acyltransferase from the lipid body fraction of an oleaginous fungus. J Biochem 121:1107-14.
29. Katavic, V., D. W. Reed, D. C. Taylor, E. M. Giblin, D. L. Barton, J. Zou, S. L. Mackenzie, P. S. Covello, and L. Kunst. 1995. Alteration of seed fatty acid composition by an ethyl methanesulfonate-induced mutation in *Arabidopsis thaliana* affecting diacylglycerol acyltransferase activity. Plant Physiol 108:399-409.
30. Kwanyuen, P., and R. F. Wilson. 1986. Isolation and purification of diacylglycerol acyltransferase from germinating soybean cotyledons. Biochim Biophys Acta 877:238-245.

31. Kwanyuen, P., and R. F. Wilson. 1990. Subunit and amino acid composition of diacylglycerol acyltransferase from germinating soybean cotyledons. Biochim Biophys Acta 1039:67-72.
32. Kwanyuen, P., R. F. Wilson, and J. W. Burton. 1988. Substrate specificity of diacylglycerol acyltransferase purified from soybean. Proceedings: World Conference on Biotechnology for the Fats and Oils Industry/edited by Thomas H. Applewhite. Champaign, Ill. American Oil Chemists' Society, c1988. p.:294-297.
33. Lardizabal, K., R. Effertz, C. Levering, J. Mai, M. C. Pedroso, T. Jury, E. Aasen, K. Gruys, and K. Bennett. 2008. Expression of *Umbelopsis ramanniana* DGAT2A in Seed Increases Oil in Soybean. Plant Physiol. 148:89-96.
34. Lardizabal, K. D., J. T. Mai, N. W. Wagner, A. Wyrick, T. Voelker, and D. J. Hawkins. 2001. DGAT2 Is a new diacylglycerol acyltransferase gene family. Purification, cloning, and expression in insect sells of two polypeptides from *Mortierella ramanniana* with diacylglycerol acyltransferase activity. J. Biol. Chem. 276:38862-38869.
35. Le, B. H., J. A. Wagmaister, T. Kawashima, A. Q. Bui, J. J. Harada, and R. B. Goldberg. 2007. Using genomics to study legume seed development. Plant Physiology 144: 562-574.
36. Lehner, R., and A. Kuksis. 1993. Triacylglycerol synthesis by an sn-1,2(2,3)-diacylglycerol transacylase from rat intestinal microsomes. J Biol Chem 268:8781-6.
37. Li, R., K. Yu, and D. Hildebrand. 2010a. DGAT1, DGAT2 and PDAT Expression in Seeds and Other Tissues of Epoxy and Hydroxy Fatty Acid Accumulating Plants. Lipids 45:145-157.
38. Li, R., K. Yu, T. Hatanaka, and D. F. Hildebrand. 2010b. *Vernonia* DGATs increase accumulation of epoxy fatty acids in oil. Plant Biotechnology Journal 8:184-195.
39. Loer, D. S., and E. M. Herman. 1993. Cotranslational integration of soybean (*Glycine max*) oil body membrane protein oleosin into microsomal membranes. Plant-physiology; March 1993; 101(3): 993-998 101:993-998.
40. Lonien, J., and J. Schwender. 2009. Analysis of Metabolic Flux Phenotypes for Two *Arabidopsis* Mutants with Severe Impairment in Seed Storage Lipid Synthesis. Plant Physiol. 151:1617-1634.
41. Lu, C., and M. J. Hills. 2002. *Arabidopsis* mutants deficient in diacylglycerol acyltransferase display increased sensitivity to abscisic acid, sugars, and osmotic stress during germination and seedling development. Plant Physiol 129:1352-1358.
42. Lu, C., Z. Xin, Z. Ren, M. Miguel, and J. Browse. 2009. An enzyme regulating triacylglycerol composition is encoded by the ROD1 gene of *Arabidopsis*. Proceedings of the National Academy of Sciences 106:18837-18842.
43. Lu, C. L., S. B. de Noyer, D. H. Hobbs, J. Kang, Y. Wen, D. Krachtus, and M. J. Hills. 2003. Expression pattern of diacylglycerol acyltransferase-1, an enzyme involved in triacylglycerol biosynthesis, in *Arabidopsis thaliana*. Plant Mol Biol 52:31-41.
44. Maeo, K., T. Tokuda, A. Ayame, N. Mitsui, T. Kawai, H. Tsukagoshi, S. Ishiguro, and K. Nakamura. 2009. An AP2-type transcription factor, WRINKLED1, of *Arabidopsis thaliana* binds to the AW-box sequence conserved among proximal upstream regions of genes involved in fatty acid synthesis. The Plant Journal 60:476-487.
45. Mhaske, V., K. Beldjilali, J. Ohlrogge, and M. Pollard. 2005. Isolation and characterization of an *Arabidopsis thaliana* knockout line for phospholipid: diacylglycerol transacylase gene (At5g13640). Plant Physiol Biochem 43:413-417.
46. Mu, J. Y., H. L. Tan, Q. Zheng, F. Y. Fu, Y. Liang, J. A. Zhang, X. H. Yang, T. Wang, K. Chong, X. J. Wang, and J. R. Zuo. 2008. LEAFY COTYLEDON1 is a key regulator of fatty acid biosynthesis in *Arabidopsis*. Plant Physiology 148:1042-1054.
47. Nosarzewski, M., and D. D. Archbold. 2007. Tissue-specific expression of SORBITOL DEHYDROGENASE in apple fruit during early development. J Exp Bot 58:1863-1872.
48. Oelkers, P., A. Tinkelenberg, N. Erdeniz, D. Cromley, J. T. Billheimer, and S. L. Sturley. 2000. A Lecithin Cholesterol Acyltransferase-like Gene Mediates Diacylglycerol Esterification in Yeast. J. Biol. Chem. 275:15609-15612.
49. Ohlrogge, J., D. Allen, B. Berguson, D. DellaPenna, Y. Shachar-Hill, and S. Stymne. 2009. Driving on Biomass. Science 324:1019-1020.
50. Ohlrogge, J. B., and J. Browse. 1995. Lipid biosynthesis. Plant Cell 7:957-970.
51. Rao, S., and D. Hildebrand. 2009. Changes in Oil Content of Transgenic Soybeans Expressing the Yeast SLC1 Gene. Lipids 44:945-951.
52. Routaboul, J.-M., C. Benning, N. Bechtold, M. Caboche, and L. Lepiniec. 1999. The TAG1 locus of *Arabidopsis* encodes for a diacylglycerol acyltransferase. Plant Physiology and Biochemistry 37:831-840.
53. Saha, S., B. Enugutti, S. Rajakumari, and R. Rajasekharan. 2006. Cytosolic Triacylglycerol Biosynthetic Pathway in Oilseeds. Molecular Cloning and Expression of Peanut Cytosolic Diacylglycerol Acyltransferase. Plant Physiology 141:1533-1543.
54. Sarmiento, C., J. H. Ross, E. Herman, and D. J. Murphy. 1997. Expression and subcellular targeting of a soybean oleosin in transgenic rapeseed. Implications for the mechanism of oil-body formation in seeds. Plant Journal 11:783-796.
55. Schmutz, J., S. B. Cannon, J. Schlueter, J. Ma, T. Mitros, W. Nelson, D. L. Hyten, Q. Song, J. J. Thelen, J. Cheng, D. Xu, U. Hellsten, G. D. May, Y. Yu, T. Sakurai, T. Umezawa, M. K. Bhattacharyya, D. Sandhu, B. Valliyodan, E. Lindquist, M. Peto, D. Grant, S. Shu, D. Goodstein, K. Barry, M. Futrell-Griggs, B. Abernathy, J. Du, Z. Tian, L. Zhu, N. Gill, T. Joshi, M. Libault, A. Sethuraman, X.-C. Zhang, K. Shinozaki, H. T. Nguyen, R. A. Wing, P. Cregan, J. Specht, J. Grimwood, D. Rokhsar, G. Stacey, R. C. Shoemaker, and S. A. Jackson. 2010. Genome sequence of the palaeopolyploid soybean. Nature 463:178-183.
56. Settlage, S. B., P. Kwanyuen, and R. F. Wilson. 1998. Relation between diacylglycerol acyltransferase activity and oil concentration in soybean. J Am Oil Chem Soc 75:775-781.
57. Shen, B., W. B. Allen, P. Zheng, C. Li, K. Glassman, J. Ranch, D. Nubel, and M. C. Tarczynski. 2010. Expression of ZmLEC1 and ZmWRI1 Increases Seed Oil Production in Maize. Plant Physiol.:pp. 110.157537.
58. Siloto, R. M. P., K. Findlay, A. Lopez-Villalobos, E. C. Yeung, C. L. Nykiforuk, and M. M. Moloney. 2006. The Accumulation of Oleosins Determines the Size of Seed Oilbodies in *Arabidopsis*. Plant Cell 18:1961-1974.
59. Slack, C. R., P. G. Roughan, J. A. Browse, and S. E. Gardiner. 1985. Some properties of choline phosphotransferase from developing safflower cotyledons. Biochim Biophys Acta 833:438-448.
60. Stahl, U., A. Carlsson, M. Lenman, A. Dahlqvist, B. Huang, W. Bana, A. Bana, and S. Stymne. 2004. Cloning and Functional Characterization of a Phospholipid:Diacylglycerol Acyltransferase from *Arabidopsis* Plant Physiol. 135:1324-1335.

61. Stobart, K., M. Mancha, M. Lenman, A. Dahlqvist, and S. S. 1997. Triacylglycerols are synthesised and utilized by transacylation reactions in microsomal preparations of developing safflower (*Carthamus tinctorius* L.) seeds. Planta 203:58-66.
62. Taylor, D. C., Z. Yan, A. Kumar, T. Francis, E. M. Giblin, D. L. Barton, J. R. Ferrie, A. Laroche, S. Shah, Z. Weiming, C. L. Snyder, L. Hall, G. Rakow, J. L. Harwood, and R. J. Weselake. 2009. Molecular modification of triacylglycerol accumulation by over-expression of DGAT1 to produce canola with increased seed oil content under field conditions. Botany 87:533-543.
63. Triki, S., J. Ben Hamida, and P. Mazliak. 1998. About the reversibility of the cholinephosphotransferase in developing sunflower seed microsomes, p. 236-239, In J. Sanchez, et al., eds. Advances in Plant Lipid Research. Univ. Sevilla, Sevilla.
64. Turkish, A. R., A. L. Henneberry, D. Cromley, M. Padamsee, P. Oelkers, H. Bazzi, A. M. Christiano, J. T. Billheimer, and S. L. Sturley. 2005. Identification of Two Novel Human Acyl-CoA Wax Alcohol Acyltransferases: MEMBERS OF THE DIACYLGLYCEROL ACYLTRANSFERASE 2 (DGAT2) GENE SUPERFAMILY. Journal of biological chemistry 280:14755-14764.
65. Tzen, J. T. C., Y. K. Lai, K. L. Chan, and A. H. C. Huang. 1990. Oleosin isoforms of high and low molecular weights are present in the oil bodies of diverse seed species. Plantphysiology 94:1282-1289.
66. USDA. 2009a. World Agricultural Supply and Demand Estimates, WASDE-477, In E. R. Service, (ed.), Washington, D.C.
67. USDA. 2009b. Oilseeds: World Markets and Trade, FOP 10-09, In F. A. Service, (ed.), Washington, D.C.
68. Vogel, G., and J. Browse. 1996. Cholinephosphotransferase and diacylglycerol acyltransferase: Substrate specificities at a key branch point in seed lipid metabolism. Plant physiol 110:923-931.
69. Vyacheslav, A., B. Nikolai, P. Natalia, B. Anita, D. Joseph, S. Sergei, F. John, M. Paulina, A. Karolina, L. Marilyn, G. Maxim, and K. Hilary. 2009. Tobacco as a production platform for bio fuel: overexpression of *Arabidopsis* DGAT and LEC2 genes increases accumulation and shifts the composition of lipids in green biomass. Plant Biotechnology Journal 8:1-11.
70. Wang, H.-W., J.-S. Zhang, J.-Y. Gai, and S.-Y. Chen. 2006. Cloning and comparative analysis of the gene encoding diacylglycerol acyltransferase from wild type and cultivated soybean. Theoretical and Applied Genetics 112:1086-1097.
71. Wang, H. W., B. Zhang, Y. J. Hao, J. Huang, A. G. Tian, Y. Liao, J. S. Zhang, and S. Y. Chen. 2007a. The soybean Dof-type transcription factor genes, GmDof4 and GmDof11, enhance lipid content in the seeds of transgenic *Arabidopsis* plants. Plant Journal 52:716-729.
72. Wang, H. Y., J. H. Guo, K. N. Lambert, and Y. Lin. 2007b. Developmental control of *Arabidopsis* seed oil biosynthesis. Planta 226:773-783.
73. Weselake, R. J., D. C. Taylor, M. H. Rahman, S. Shah, A. Laroche, P. B. E. McVetty, and J. L. Harwood. 2009. Increasing the flow of carbon into seed oil. Biotechnology Advances 27:866-878.
74. Wilson, R. F., and D. Hildebrand. 2010. Engineering Status, Challenges and Advantages of Oil crops, In P. Mascia, et al., eds. Plant Biotechnology for Sustainable Production of Energy and Coproducts. Springer.
75. Yu, K., R. Li, T. Hatanaka and D. Hildebrand. 2008. Cloning and functional analysis of two type 1 diacylglycerol acyltransferases from *Vernonia galamensis*, Phytochemistry 69:1119-1127.
76. Zhang, F.-Y., M.-F. Yang, and Y.-N. Xu. 2005. Silencing of DGAT1 in tobacco causes a reduction in seed oil content. Plant science 169:689-694.
77. Zhang, M., J. Fan, D. C. Taylor, and J. B. Ohlrogge. 2009. DGAT1 and PDAT1 Acyltransferases Have Overlapping Functions in *Arabidopsis* Triacylglycerol Biosynthesis and Are Essential for Normal Pollen and Seed Development. Plant Cell 21:3885-3901.
78. Zou, J., Y. Wei, and D. C. Taylor. 1999. The *Arabidopsis thaliana* TAG1 mutant has a mutation in a diacylglycerol acyl transferase gene. Plant Journal 19:645-654.
79. Zou, J. T., V. Katavic, E. M. Giblin, D. L. Barton, S. L. MacKenzie, W. A. Keller, X. Hu, and D. C. Taylor. 1997. Modification of seed oil content and acyl composition in the Brassicaceae by expression of a yeast sn-2 acyltransferase gene. Plant Cell 9:909-923.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of increasing renewable oil production in a plant, comprising transforming a plant cell with an isolated nucleic acid encoding a *Vernonia galamensis* diacylglycerol acyltransferase 1 (VgDGAT1) polypeptide, wherein expression of the VgDGAT1 polypeptide increases the total amount of renewable oil in the plant relative to a control plant that is not transformed with the isolated nucleic acid encoding the VgDGAT1 polypeptide.

2. The method of claim 1, wherein the increase in the total amount of renewable oil in the plant is at least about a 2 percent increase as compared to an amount of renewable oil in the control plant.

3. The method of claim 1, wherein the increase in the total amount of renewable oil in the plant is at least about a 5 percent increase as compared to an amount of renewable oil in the control plant.

4. The method of claim 1, wherein the plant is selected from the group consisting of *Arachis hypogaea, Borago officinalis, Brassica campestris, Brassica napus, Brassica rapa, Camelina sativa, Cannabis sativa, Carthamus tinctorius, Cocos nucifera, Crambe abyssinica, Cuphea* species, *Glycine max, Gossypium hirsutum, Gossypium barbadense, Gossypium herbaceum, Helianthus annuus, Linum usitatissimum, Oenothera biennis, Olea europaea, Oryza sativa, Perilla frutescens, Ricinus communis, Salvia hispanica, Sesamum indicum, Sinapis alba, Theobroma cacao, Triticum* species, *Zea mays, Juglans* species, and *Prunis dulcis*.

5. The method of claim 1, wherein increasing the total amount of renewable oil in the plant relative to the control plant comprises increasing the total amount of renewable oil in a seed of the plant.

6. The method of claim 1, wherein increasing the total amount of renewable oil in the plant relative to the control plant comprises increasing the amount of triacylglycerol (TAG) in the plant.

7. The method of claim 1, wherein a total amount of protein in the plant is about equal to a total amount of protein in the control plant.

8. The method of claim 1, wherein a total amount of protein in the plant is increased relative to the control plant.

9. The method of claim 1, wherein the VgDGAT1 polypeptide is a VgDGAT1a polypeptide.

10. The method of claim 9, wherein the VgDGAT1a polypeptide is encoded by a nucleic acid molecule having the sequence of SEQ ID NO: 1.

11. The method of claim 9, wherein the VgDGAT1a polypeptide comprises the amino acid sequence of SEQ ID NO: 2.

12. The method of claim 1, wherein the VgDGAT1 polypeptide is a VgDGAT1b polypeptide.

13. The method of claim 12, wherein the VgDGAT1b polypeptide is encoded by a nucleic acid molecule having the sequence of SEQ ID NO: 3.

14. The method of claim 12, wherein the VgDGAT1b polypeptide comprises the amino acid sequence of SEQ ID NO: 4.

15. The method of claim 1, further comprising transforming a plant cell with an isolated nucleic acid encoding a *Vernonia galamensis* diacylglycerol acyltransferase 2 (VgDGAT2) polypeptide, wherein expression of the VgDGAT1 polypeptide and the VgDGAT2 polypeptide increases a total amount of renewable oil in the plant relative to a control plant that is not transformed with the isolated nucleic acid encoding the VgDGAT2 polypeptide.

16. The method of claim 15, wherein the VgDGAT2 polypeptide is encoded by a nucleic acid molecule having the sequence of SEQ ID NO: 5.

17. The method of claim 15, wherein the VgDGAT2 polypeptide comprises the amino acid sequence of SEQ ID NO: 6.

18. A method of producing a triacylglycerol (TAG), comprising transforming a cell with an isolated nucleic acid that encodes a *Vernonia galamensis* diacylglycerol acyltransferase 1 (VgDGAT1) polypeptide, wherein expression of the VgDGAT1 polypeptide increases the total amount of TAG in the cell relative to a control cell that is not transformed with the isolated nucleic acid encoding the VgDGAT1 polypeptide.

19. The method of claim 18, wherein the transformed cell is an animal cell, a plant cell, an algal cell, a fungal cell, or a yeast cell.

20. A transgenic plant cell comprising an isolated nucleic acid encoding a *Vernonia galamensis* diacylglycerol acyltransferase 1 (VgDGAT1) polypeptide, wherein expression of the VgDGAT1 polypeptide increases the total amount of renewable oil in the plant cell relative to a control cell that is not transformed with the isolated nucleic acid encoding the VgDGAT1 polypeptide.

21. The transgenic plant cell of claim 20, wherein the isolated nucleic acid is operably linked to an expression control sequence.

22. The transgenic plant cell of claim 21, wherein the expression control sequence comprises a constitutive promoter or a seed-specific promoter.

23. A method of increasing renewable oil production in a plant, comprising transforming a plant cell with a first isolated nucleic acid encoding a *Vernonia galamensis* diacylglycerol acyltransferase (VgDGAT) polypeptide and a second isolated nucleic acid encoding an epoxygenase polypeptide, wherein expression of the VgDGAT polypeptide and the epoxygenase polypeptide increases an amount of renewable oil in the plant.

24. The method of claim 23, wherein the VgDGAT polypeptide is a VgDGAT1a polypeptide.

25. The method of claim 24, wherein the VgDGAT1a polypeptide is encoded by a nucleic acid molecule having the sequence of SEQ ID NO: 1.

26. The method of claim 24, wherein the VgDGAT1a polypeptide comprises the amino acid sequence of SEQ ID NO: 2.

27. The method of claim 23, wherein the VgDGAT polypeptide is a VgDGAT1b polypeptide.

28. The method of claim 27, wherein the VgDGAT1b polypeptide is encoded by a nucleic acid molecule having the sequence of SEQ ID NO: 3.

29. The method of claim 27, wherein the VgDGAT1b polypeptide comprises the amino acid sequence of SEQ ID NO: 4.

30. The method of claim 23, wherein the VgDGAT polypeptide is a VgDGAT2 polypeptide.

31. The method of claim 30, wherein the VgDGAT2 polypeptide is encoded by a nucleic acid molecule having the sequence of SEQ ID NO: 5.

32. The method of claim 30, wherein the VgDGAT2 polypeptide comprises the amino acid sequence of SEQ ID NO: 6.

33. The method of claim 23, wherein the epoxygenase polypeptide is encoded by a nucleic acid sequence comprising the sequence of SEQ ID NO: 19.

34. The method of claim 23, wherein an amount of protein in the plant is substantially unchanged as compared to a control plant.

35. The method of claim 23, wherein an amount of protein in the plant is increased as compared to a control plant.

* * * * *